United States Patent
Bilton et al.

(10) Patent No.: US 10,194,730 B2
(45) Date of Patent: Feb. 5, 2019

(54) METHOD OF CONTROLLING PERSPIRATION

(71) Applicant: Conopco, Inc., Englewood Cliffs, NJ (US)

(72) Inventors: Simon Lewis Bilton, Leamington Spa (GB); Christopher John Jones, Tewkesbury (GB); Rebecca Anne Nelson, Bristol (GB); Benjamin George Oglesby, Leeds (GB); Guy Richard Thompson, Parkgate (GB); Iain Andrew Weddell, Chester (GB)

(73) Assignee: Conopco, Inc., Englewood Cliffs, NJ (US)

( * ) Notice: Subject to any disclaimer, the term of this patent is extended or adjusted under 35 U.S.C. 154(b) by 108 days.

(21) Appl. No.: 15/517,340

(22) PCT Filed: Oct. 13, 2015

(86) PCT No.: PCT/EP2015/073706
§ 371 (c)(1),
(2) Date: Apr. 6, 2017

(87) PCT Pub. No.: WO2016/062586
PCT Pub. Date: Apr. 28, 2016

(65) Prior Publication Data
US 2017/0245623 A1  Aug. 31, 2017

(30) Foreign Application Priority Data
Oct. 24, 2014 (EP) .................................. 14190348

(51) Int. Cl.
A45D 40/26 (2006.01)
A61Q 15/00 (2006.01)
(Continued)

(52) U.S. Cl.
CPC ............. *A45D 40/26* (2013.01); *A45D 34/04* (2013.01); *A61K 8/41* (2013.01); *A61Q 15/00* (2013.01); *A61K 2800/87* (2013.01)

(58) Field of Classification Search
CPC ........ A45D 40/26; A45D 34/04; A45D 34/00; A45D 40/02; A61Q 15/00; A61K 8/41;
(Continued)

(56) References Cited

U.S. PATENT DOCUMENTS

| 5,255,990 A | 10/1993 | Dornbusch et al. |
| 5,336,005 A | 8/1994 | Moeck |

(Continued)

FOREIGN PATENT DOCUMENTS

| EP | 0108636 | 5/1984 |
| EP | 0312165 | 4/1989 |

(Continued)

OTHER PUBLICATIONS

IPRP2 in PCTEP2015073699, Jan. 4, 2017.
(Continued)

*Primary Examiner* — David Walczak
(74) *Attorney, Agent, or Firm* — Greenberg Traurig, LLP

(57) ABSTRACT

An antiperspirant composition and a dispenser therefor, the composition being a gel, cream or soft solid of viscosity from 3000 mPa·s to 5200 mPa·s at a shear rate of 16/s comprising a non-pore blocking inhibitor of perspiration and the dispenser comprising a dome-shaped applicator surface of radius of curvature decreasing from a maximum of from 25 to 60 mm at its top/center to a value of from 75 to 95% of its maximum value at a distance of 1 cm from its top/center.

19 Claims, 17 Drawing Sheets

(51) Int. Cl.
*A61K 8/41* (2006.01)
*A45D 34/04* (2006.01)

(58) Field of Classification Search
CPC .. A61K 2800/87; B05C 17/00; B05C 17/005; B05C 17/00503; B05C 17/01
See application file for complete search history.

(56) References Cited

U.S. PATENT DOCUMENTS

| | | | |
|---|---|---|---|
| 6,071,027 | A | 6/2000 | Gueret |
| 7,901,152 | B2 * | 3/2011 | Hines ................. A47L 25/08 401/172 |
| 8,517,622 | B2 * | 8/2013 | Apodaca ............. A45D 40/26 401/183 |
| 8,618,160 | B2 | 12/2013 | Johnston et al. |
| 8,777,505 | B2 * | 7/2014 | Thorez ................ A45D 40/26 401/186 |
| 2008/0207737 | A1 | 8/2008 | Zinger |
| 2010/0104612 | A1 | 4/2010 | Cropper et al. |
| 2010/0114025 | A1 | 5/2010 | Moller |
| 2010/0217176 | A1 | 8/2010 | Carrara et al. |
| 2014/0154197 | A1 | 6/2014 | Swaile et al. |

FOREIGN PATENT DOCUMENTS

| | | |
|---|---|---|
| EP | 2243720 | 10/2010 |
| GB | 2472412 | 2/2011 |
| WO | WO0211690 A1 | 2/2002 |
| WO | WO2010081205 | 7/2010 |
| WO | WO2011039236 | 4/2011 |
| WO | WO2012131320 | 10/2012 |

OTHER PUBLICATIONS

Search Report in EP14190348, dated Apr. 21, 2015.
Search Report in EP14190349, dated Mar. 31, 2015.
Search Report in EP14190350, dated Apr. 21, 2015.
Search Report in PCTEP2015073699, dated Dec. 23, 2015.
Search Report in PCTEP2015073706, dated Nov. 3, 2015.
Written Opinion in EP14190348, dated Apr. 21, 2015.
Written Opinion in EP14190349, dated Mar. 31, 2015.
Written Opinion in EP14190350, dated Apr. 21, 2015.
Written Opinion in PCTEP2015073699, dated Dec. 23, 2015.
Written Opinion in PCTEP2015073706, dated Nov. 3, 2015.
Co-Pending Application, Simon Lewis Bilton, U.S. Appl. No. 15/517,361, filed Apr. 6, 2017.
IPRP1 in PCTEP2015073706; Apr. 25, 2017.

* cited by examiner

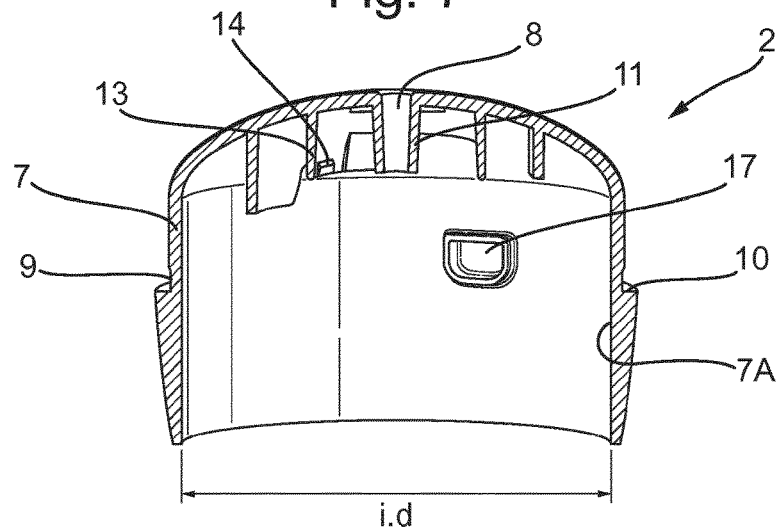
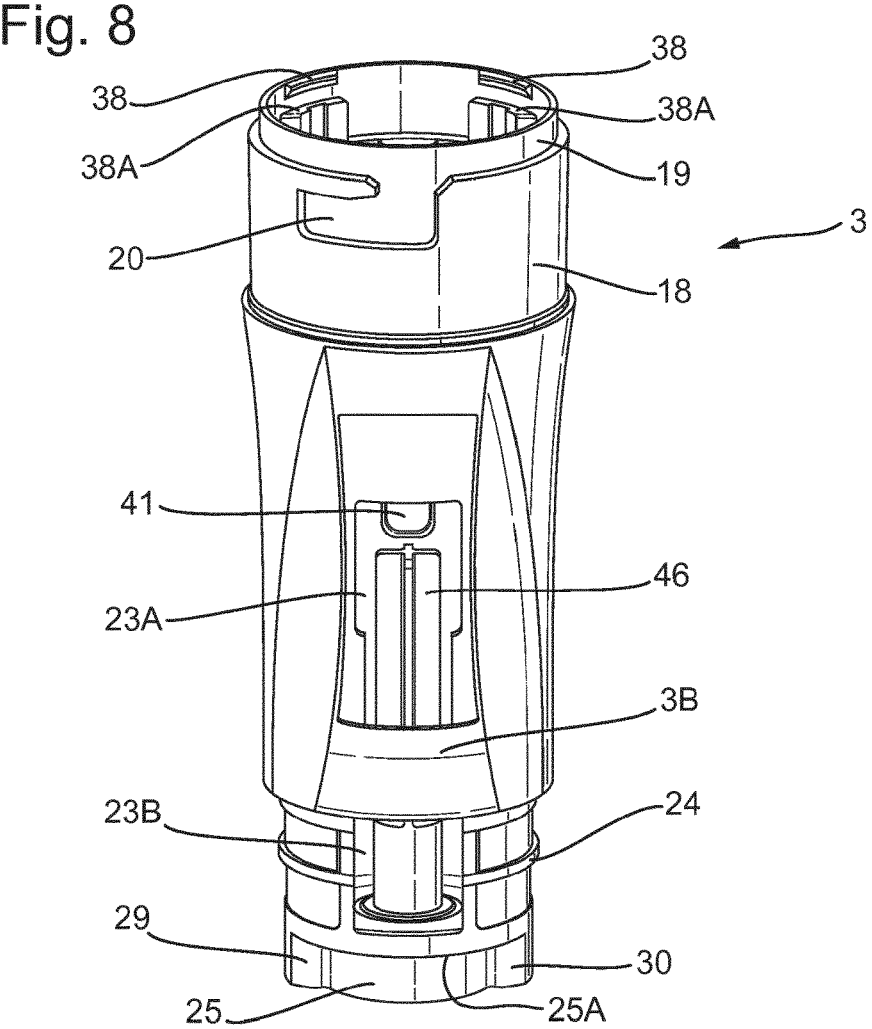

METHOD OF CONTROLLING PERSPIRATION

The present invention is in the field of antiperspirancy. The invention is particular concerned with the control of perspiration from the human body and with compositions and dispensers for achieving this.

There have been numerous methods devised for the treatment of perspiration. In recent years, the method of choice in the market has been the use of astringent salts of aluminium and/or zirconium, such as aluminium chlorohydrate. Such materials function by blocking the sweat ducts and thereby reducing the amount of perspiration making its way onto the surface of the human body.

There have also been numerous dispensers devised for use in applying cosmetic compositions, including antiperspirants, which are creams, gels or soft solids.

EP 2,243,720 A1 (Nossbaum et al, 2010) discloses an apparatus for dispensing viscous substances having a drive mechanism comprising a drive nut and an expulsion member comprising a plunger. The apparatus is suitable for use with toothpaste or soap.

U.S. Pat. No. 5,336,005 (Schwan Stabilo Schwanhaeusser, 1994) discloses an applicator device for a spreadable stick material axially displaced by a screwthreaded spindle. The screwthreaded spindle is returned to its start position by a spring when the front end of the applicator is removed.

U.S. Pat. No. 6,071,027 (L'Oreal, 2000) discloses an applicator holder device comprising a pusher mechanism that can be actuated so as to pass from a rest position to an active position. The pusher mechanism drives an applicator in an axial duct and can be returned to its rest position when the head is removed from the holder.

Methods of treating perspiration at its source, i.e. reducing sweat production from sweat glands, in particular the secretory coils of the eccrine glands, have been less commonly reported.

WO 02/011690 (Unilever) discloses an antiperspirancy method whereby calcium channels with the secretory coil cells of the eccrine glands are blocked, thereby controlling sweat production at its source.

U.S. Pat. No. 8,618,160 B2 (Rose U) discloses wipes containing glycopyrrolate, a muscarinic anticholinergic, as a treatment for hyperhidrosis.

Certain anticholinergic drugs have also been used to treat hyperhidrosis, with varying degrees of success. These drugs include Ditropan® (oxybutynin), Probanthine® (propantheline bromide) and Cogentin® (benzotropine).

US 2008/0207737 (Zinger) discloses a topical composition for antiperspirant benefit and comprising varying levels of oxybutynin.

The present invention enables the control of human perspiration by the topical delivery of a non-pore blocking inhibitor of perspiration. Further, said topical delivery may be achieved without the user having finger contact with the non-pore blocking inhibitor of perspiration. This is more convenient for the consumer and more hygienic.

The invention typically works by reducing sweat production at its source, i.e., the secretory coils of the sweat glands, in particular the eccrine glands.

In a first aspect of the invention, there is provided a product comprising a composition and a dispenser therefor, the composition being a gel, cream or soft solid of viscosity from 3000 mPa·s to 5200 mPa·s at a shear rate of 16/s comprising a non-pore blocking inhibitor of perspiration and the dispenser comprising a dome-shaped applicator surface of radius of curvature decreasing from a maximum of from 25 to 60 mm at its top/centre to a value of from 75 to 95% of its maximum value at a distance of 1 cm from its top/centre.

In a second aspect of the invention, there is provided a product according to the first aspect of the invention for use in treating perspiration, in particular excessive perspiration.

For the avoidance of doubt, this second aspect of the invention includes possible cosmetic, medicinal or pharmaceutical use.

In a third aspect of the invention, there is provided a cosmetic method of controlling perspiration, in particular excessive perspiration, wherein the method comprises the use of a product according to the first aspect of the invention.

The third aspect of the invention may be alternatively worded as the provision of a cosmetic method of controlling perspiration, in particular excessive perspiration, wherein the method comprises the application of a composition comprising a non-pore blocking inhibitor of perspiration using a dispenser comprising a dome-shaped applicator surface of radius of curvature decreasing from a maximum of from 25 to 60 mm at its top/centre to a value of from 75 to 95% of its maximum value at a distance of 1 cm from its top/centre.

In a fourth aspect of the invention, there is provided a method of manufacture of a dispenser suitable for use in any of the aforementioned aspects of the invention.

Herein, a cosmetic method means a method involving a cosmetic treatment and/or a cosmetic composition, such treatment or composition not involving medicinal or pharmaceutical components.

Herein, excessive sweating should be understood to refer to that condition known as hyperhidrosis.

The methods and treatments of the present invention are of greatest benefit when used on the surface of the human body, i.e. on the skin of the human body. They are of particular value when used in the underarm areas of the human body. The dispenser used as part of the present invention is designed to be particularly effective when used in the underarm areas of the human body. One of the features of the invention relevant to the latter area of application is the dome-shaped applicator surface of the dispenser.

In accordance with the present invention, the dispenser used as part of the present invention topically delivers a non-pore blocking inhibitors of perspiration.

Preferred non-pore blocking inhibitors of perspiration are anti-cholinergic substances, such as oxybutynin.

By use of the particular viscosities of composition and radii of curvature of the dome-shaped applicator surface, the inventors have found that optimum delivery of gels, creams or soft solids comprising a non-pore blocking inhibitor of perspiration may be achieved.

The combined compositional and applicator features of the invention enable the composition to be retained on the applicator surface extremely well and to be delivered with high efficiency. Without wishing to be bound by theory, it is believed that these features enhance delivery of the non-pore blocking inhibitor of perspiration to its target, which is typically eccrine glands located beneath the skin surface, particularly in the underarm regions. Delivery of non-pore blocking inhibitors of perspiration that are anti-cholinergic agents is particularly efficient by use of the present invention.

The non-pore blocking inhibitor of perspiration is preferably an anti-cholinergic agent and is more preferably oxybutynin.

The compositions used to deliver the composition non-pore blocking inhibitor of perspiration is a gel, cream or soft solid of viscosity from 3000 mPa·s to 5200 mPa·s at a shear rate of 16/s. Preferably, the composition has a viscosity of from 3500 mPa·s to 5000 mPa·s and more preferably from 4000 mPa·s to 4600 mPa·s.

The shear rate of 16/s equates to that to which the composition is typically subjected to as it is extruded onto the convex applicator surface and is highly relevant to the flow properties of the composition at this time and immediately thereafter.

It is further preferred that the compositions have a viscosity of from 60 mPa·s to 80 mPa·s at a shear rate of 4240/s and more preferably of viscosity from 64 mPa·s to 74 mPa·s at a shear rate of 4240/s. The shear rate of 4240/s equates to that to which the composition is typically subjected to it is transferred from the convex applicator surface onto the surface of the human body and is highly relevant to the flow properties of the composition at this time.

Herein, viscosities are as measured at 25° C. and 1 atmosphere pressure.

Herein, dispensers according to the invention may be equally considered to be "applicators", since their intended function is both dispensing and application of the composition contained within.

Herein "application" should be considered to refer to application to the surface of the human body, unless otherwise indicated.

Herein, application to the surface of the human body is preferably done directly. It is particularly preferred that application does not involve contact of the composition to be applied with the fingers of the person performing the application.

Herein, "unit dose" should be understood to mean a dose fixed in quantity by the dispenser/applicator. Preferably, the quantity of unit dose cannot be adjusted by the user, thereby limiting the quantity dispensed to multiples of the unit dose. The fixing of the dose quantity, especially when this dose cannot be adjusted by the user, aids the control of the treatment of the individual requiring the use of the invention.

The dome-shaped applicator surface at the upper end of the dispenser is of particular value for the application of creams, gels, and soft solids having the viscosities indicated to the underarm regions, especially for such compositions having the viscosities within the preferred ranges. This is true because such compositions spread well on the applicator surface, but are retained thereby, enabling their effective massage into the skin of the underarms. The dome-shaped applicator surface is of the shape specified, to enhance these benefits.

The dome-shaped applicator surface has a radius of curvature decreasing from a maximum of from 25 to 60 mm at its top/centre to a value of from 75 to 95% of its maximum value at a distance of 1 cm from its top/centre. Preferably, the radius of curvature of the dome-shaped applicator surface decreases to a value of from 10 to 25% of its maximum at a distance between 1.5 cm and 2.5 cm from its top/centre. The dimensions enhance the spreading and retention of the composition as well as its application to the underarm regions of the human body.

It is preferred that the radius of curvature of the applicator surface decreases at the same rate and to the same extent in whichever direction one travels radially outwards from its top/centre.

Herein, "dome-shaped" refers to three-dimensional convex surfaces and is not restricted to dome surfaces that have the shape of the outer surface of part of a sphere; indeed, such surfaces are excluded by the varying radius of curvature requirement.

Herein, the top/centre of the dome is at its top and is centrally located in a radial, i.e., horizontal, plane.

Herein, distances indicated as being from the top/centre of the dome are measured as minimum distances along the dome surface.

The diameter of the dome-shaped applicator surface is typically from 3 cm to 6 cm, this enhancing delivery of the composition to the skin, particularly in the underarm regions and delivery of the inhibitor of perspiration to its target.

In preferred embodiments, the domed shaped applicator surface is smooth, i.e. it does not have indentations or protrusions such as ridges or lumps.

It is highly preferred that the applicator surface comprises an aperture for release of the composition from an internally contained reservoir. In preferred embodiments, the aperture is centrally located at the top of the dome-shaped applicator surface, i.e. it is at the top/centre of the dome.

In certain embodiments, the applicator surface comprises multiple apertures for release of the composition from an internally contained reservoir. Such embodiments can ease the flow of the composition onto the applicator surface.

The internally contained reservoir described in the paragraph immediately above is preferably a replaceable refill cartridge, preferably having a capacity of from 1 to 50 ml, more preferably from 2 to 15 ml and most preferably from 2 to 10 ml.

The applicator surface is preferably covered by a removable over-cap. This is of benefit in reducing potential evaporative loss from the composition to be dispensed, which can in turn aid its viscosity stability and flow properties. These benefits are further enhanced when the over-cap has a dimple on its inner surface that presses against a dispensing aperture in the applicator surface when the over-cap is in place.

When employed, the replaceable cartridge sits within the dispenser. It has a body, typically cylindrical in shape, and a piston seal at its base.

It is highly preferred that there is a passageway providing a means for transferring the composition in the refill cartridge to the applicator surface. The passageway has a minimum cross-sectional area that is preferably at least 1.0 mm$^2$, more preferably at least 1.5 mm$^2$, and most preferably at least 3.0 mm$^2$.

Herein, the "minimum cross-sectional area of the passageway" is the minimum cross-sectional area of the passageway along its entire length, from the cartridge to the applicator surface. This dimension may alternatively be considered to be the minimum aperture area of the passageway.

The minimum aperture areas discussed above are of relevance because of their effect upon the delivery of the composition. Compositions intended for application by dispensers of the present invention have a viscosity that makes it difficult for them to pass through narrow orifices. For this reason, the passageway between the cartridge and the applicator surface must not be too narrow. It should be clear that the higher the viscosity of the composition, particularly when the viscosity is from . . . to . . . , the more important it is to have a passageway of minimum cross-sectional area of preferably at least 1.0 mm$^2$, more preferably at least 1.5 mm$^2$, and most preferably at least 3.0 mm$^2$.

Possible problems encountered when the passageway is too narrow include high pressures within the cartridge and passageway, leading to possible leakage, slow dispensing of the composition onto the applicator surface and shear-thinning of composition as it passes through the passageway, leading to its poor retention on the applicator surface.

In preferred embodiments, the dispenser comprises a drive mechanism comprising a dial unit and a plunger. The drive mechanism serves to force the compositions from the replaceable cartridge, though the passageway, and onto to the convex applicator surface.

In such embodiments, rotation of the dial unit in a first direction typically causes the plunger to advance axially upwards. The plunger acts upon a piston seal at the base of the replaceable cartridge and when it is so advanced, it forces the piston seal upwards and the composition exits the cartridge and flows onto the applicator surface, via the passageway between the two.

The dial unit typically sits at the base of the dispenser.

Rotation of the dial unit in a second direction, counter to the first, typically re-sets the dial unit relative the plunger in readiness for a further advancement of the plunger. Importantly, rotation in the second direction does not cause significant axial movement of the plunger. Preferably, rotation of the dial unit in the second direction does not cause significant rotational movement of the plunger.

Herein, "significant axial movement of the plunger" should be understood to refer to movement by greater than 5% of length of the plunger.

Herein, "significant rotational movement" should be understood to mean rotation of 10° or more.

In preferred embodiments, rotation of the dial unit in the second direction does not cause rotational movement of the plunger by 5° or more. In particularly preferred embodiments, rotation of the dial unit in the second direction does not cause any rotational movement of the plunger.

It is advantageous to restrict rotational movement of the plunger during the rotation of the dial unit in the second direction since it simplifies the drive mechanism and makes it more robust.

In preferred embodiments, rotation of the dial unit in the second direction is brought about by a torsion spring that forces the dial unit back to its start position when torque applied to turn it in its first direction is released. This feature greatly enhances the ease of use of the dispenser.

In preferred embodiments, the first rotational direction of the dial unit is counter-clockwise and the second rotational direction is clockwise.

Herein, the terms "clockwise" and "counter-clockwise" should be understood to relate to the dispenser and/or its components when viewed from above.

In preferred embodiments, rotation of the dial unit is restricted by stop faces, these faces abutting one another at the farthest rotation of the dial unit in its first direction and restricting rotational movement to preferably less than 180°, more preferably less than 120° and most preferably to between 45° and 120°.

The stop faces, when employed, preferably function between one or more features rotationally linked to the dial unit and one or more features on the plunger.

In preferred embodiments, an "advancing" ratchet which is rotationally locked to the dial unit interacts with "advancing" teeth on the plunger to cause the plunger to be raised axially upwards when the dial unit is rotated in its first direction The advancing ratchet interacts with the advancing teeth by contact of its upper surface with lower surfaces of the advancing teeth.

The advancing teeth on the plunger, preferably protrude from its outer surface and slope helically downwards around the outer surface of the plunger in the first direction, this "first direction" being the same as that previously referred to with reference to the rotation of the dial unit. The teeth are stacked equidistantly one above the other, each sloping around the outer surface of the plunger.

In preferred embodiments, there is a second "non-return" ratchet rotationally locked to the dial unit which interacts with a second set of "non-return" teeth on the plunger to prevent significant downward movement of the plunger when the dial unit is rotated in its second direction.

When present, the non-return teeth on the plunger protrude from the outer surface thereof and each tooth is in a horizontal plane, the teeth being stacked equidistantly one above another in the set.

In embodiments comprising non-return teeth as described above, it is preferred that rotation of the dial unit in its second direction does not cause axial movement of the plunger that is greater than 50% of the axial distance between the non-return teeth.

To aid efficient functioning of the drive mechanism, it is preferred that the axial distance between the advancing teeth and the non-return teeth is approximately equal.

In preferred embodiments, the non-return teeth on the plunger sit on a section raised radially above a section bearing the advancing teeth In particularly robust embodiments, there are two raised sections bearing non-return teeth diagonally opposed and separated by two lower sections bearing advancing teeth, the teeth being as described in the preceding paragraphs. In such embodiments, there are also two diagonally opposed non-return ratchets designed to interact with the non-return teeth and two advancing ratchets designed to interact with the non-return teeth, each ratchet being as described in the preceding paragraphs and preferably having the optional/preferred features also described.

In order to enhance the efficient functioning of the drive mechanism, it is preferred that the non-return ratchet(s) is/are capable of snapping over the next lower non-return tooth on the plunger when said non-return tooth is raised, together with the plunger, by the advancing ratchet(s).

In order to enhance the efficient functioning of the drive mechanism, it is preferred that the advancing ratchet(s) is/are capable of snapping over the next lower advancing tooth on the plunger when the dial unit is rotated in its second direction.

In preferred embodiments, the advancing ratchet(s) and non-return ratchet(s) are part of a ratchet sleeve, which is moulded independently of the dial unit, but slotted into the dial unit in a rotationally fixed manner during assembly of the dispenser. This arrangement eases manufacture of the dispenser.

The replaceable cartridge is preferably held in a holding unit or "refill holder" within the cylindrical body.

The outer body preferably contains a dose counter, readings on which may be seen through a window in the said body. The dose counter is preferably axially fixed to a plunger, as described above, such that it rises and falls in together with the plunger.

In preferred embodiments, the plunger as described above undergoes a rotational movement to allow disengagement from the drive mechanism and resetting of the plunger in readiness for the loading of a new replaceable cartridge. Such rotation is relative to the outer body and relative to the drive mechanism. In performing this rotational movement, the plunger drops back to its start position, preferably under the influence of a reset spring. When employed, the reset spring is typically a compression spring, preferably acting between the plunger and a holding unit for the replaceable cartridge.

The rotational movement of the plunger referred to above is preferably brought about by the rotation of an applicator head bearing the applicator surface. It is further preferred that this rotation allows for separation of the applicator head from the cylindrical body and the replacement of the cartridge contained within.

An applicator head that bears the applicator surface and that may be removed and replaced is a highly preferred feature of the dispensers according to the invention. The applicator head is preferably reversibly held onto the cylindrical body by means of one or more (preferably two) bayonet lugs on the applicator head slotting into corresponding bayonet tracks on the cylindrical body or vice versa.

In preferred embodiments, the removable applicator head as described in the paragraph immediately above comprises means for lifting the replaceable cartridge from the cylindrical body or from a refill holder within the cylindrical body. This enables the refill cartridge (12) to be removed from the refill holder (39) without the consumer needing to touch the potentially exposed composition at end of the refill cartridge (12). Typical means for lifting the replaceable cartridge are clips on a projection from the underside of the applicator head interacting with a retaining lip on the cartridge to give a light axial binding between the two.

Having a removable applicator head that comprises means for lifting the replaceable cartridge from the cylindrical body or from a refill holder within the cylindrical body is particularly beneficial when the cartridge contains a composition comprising an ingredient that it undesirable to get on the fingers of one's hand. This is particularly the case with ingredients that are non-pore blocking inhibitors of perspiration, because such ingredients are designed to permeate through the skin and could have undesirable effects, whether locally or systemically, if absorbed through the skin of the fingers.

When rotation of an applicator head brings about rotational movement of the plunger, this is preferably done by interaction of the applicator head with a holding unit for the replaceable cartridge, the holding unit being splined to the plunger to prevent rotational movement therebetween.

The interaction between the applicator head and the holding unit for the replaceable cartridge enabling the former to rotate the latter is preferably brought about by engagement tabs of the former fitting within engagement pockets of the latter, or vice versa.

Herein, references to rotation of the dial unit are relative to the outer body of the dispenser and also relative to the plunger during the first and second rotational movements referred to in the first aspect of the invention.

Herein, references to axial movement of the plunger are relative to the outer body of the dispenser and also to the body of the replaceable cartridge, when present within the dispenser.

Herein, orientation terms such as "top" and "bottom", "upwards" and "downwards", "upper" and "lower", "vertical" and "horizontal", should be understood to relate to the dispenser and/or its components when the dispenser is upright on a horizontal surface with the applicator head upmost, unless otherwise indicated. The "front" of the dispenser (1) should be understood to relate the (curved) face bearing the dose counter (22) described hereinbelow. The term "base" should be understood to have the same meaning as the term "bottom", unless otherwise indicated.

It is preferred that the convex applicator surface is part of an applicator head that may be removed and replaced.

There now follows a detailed description of a dispenser suitable for use as part of the present invention. The Figures illustrate features of this specific dispenser, but it should be understood that each feature as described in detail herein is independently a preferred feature of dispensers used in accordance with the invention as defined in the claims.

FIG. 7 is a cross-section through the applicator head (2).

Figure 9:
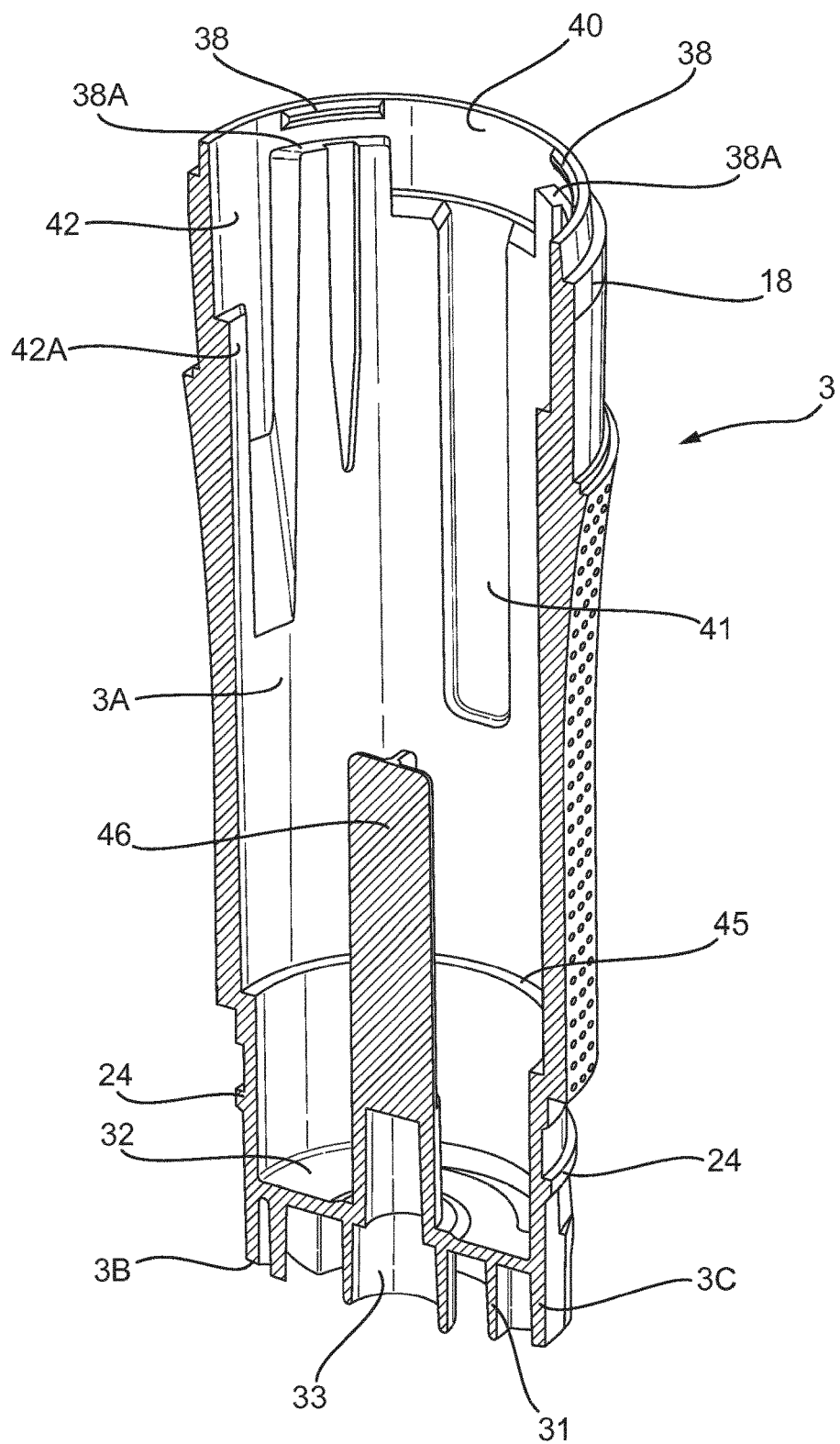
Figure 10:
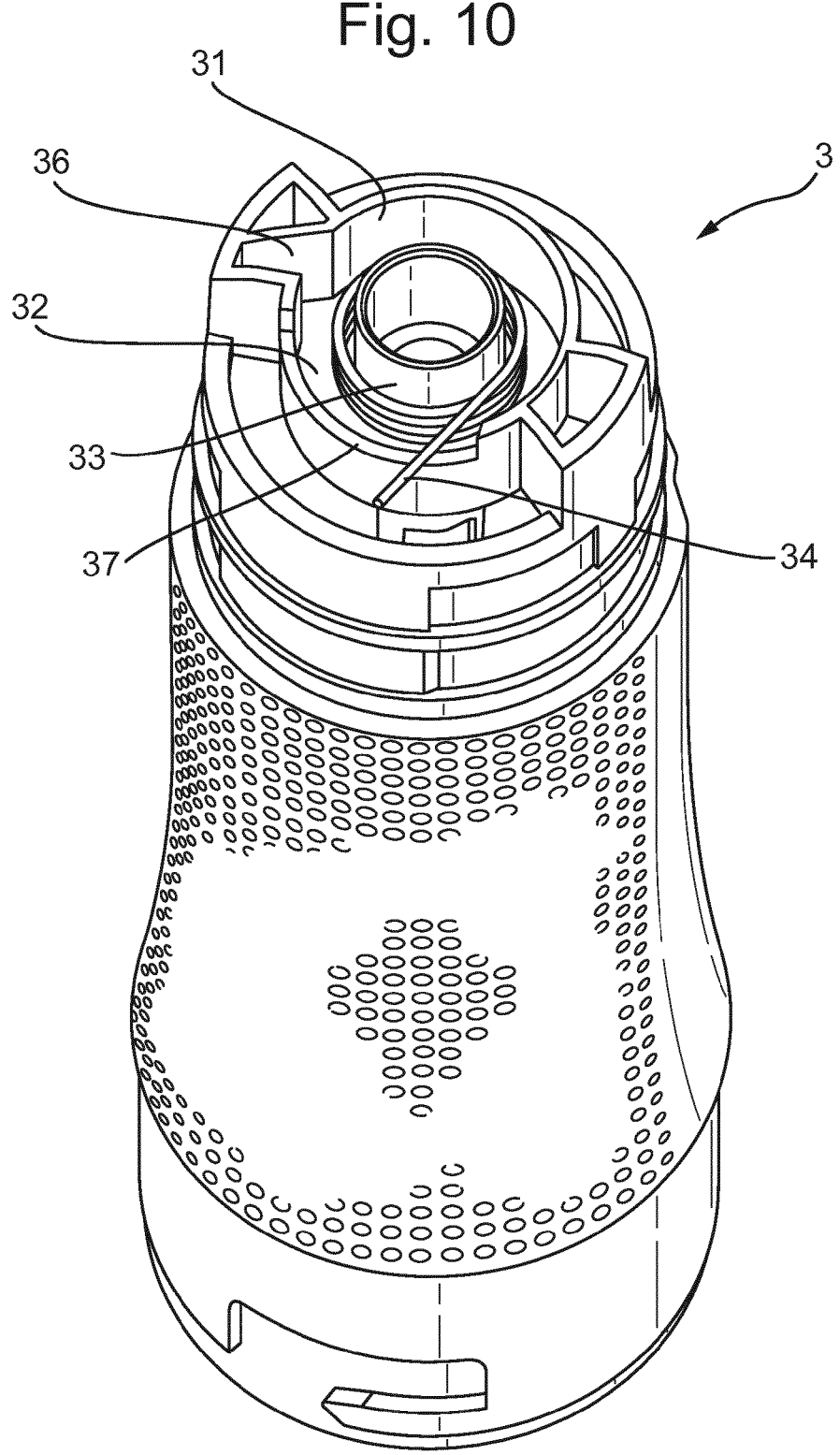

FIGS. 8, 9, and 10 illustrate the cylindrical body (3). FIG. 8 is a slightly elevated view from the front; FIG. 9 is a somewhat skewed lengthways cross-section and FIG. 10 is a view from the side and bottom and also illustrates the dial spring (34).

Figure 11:
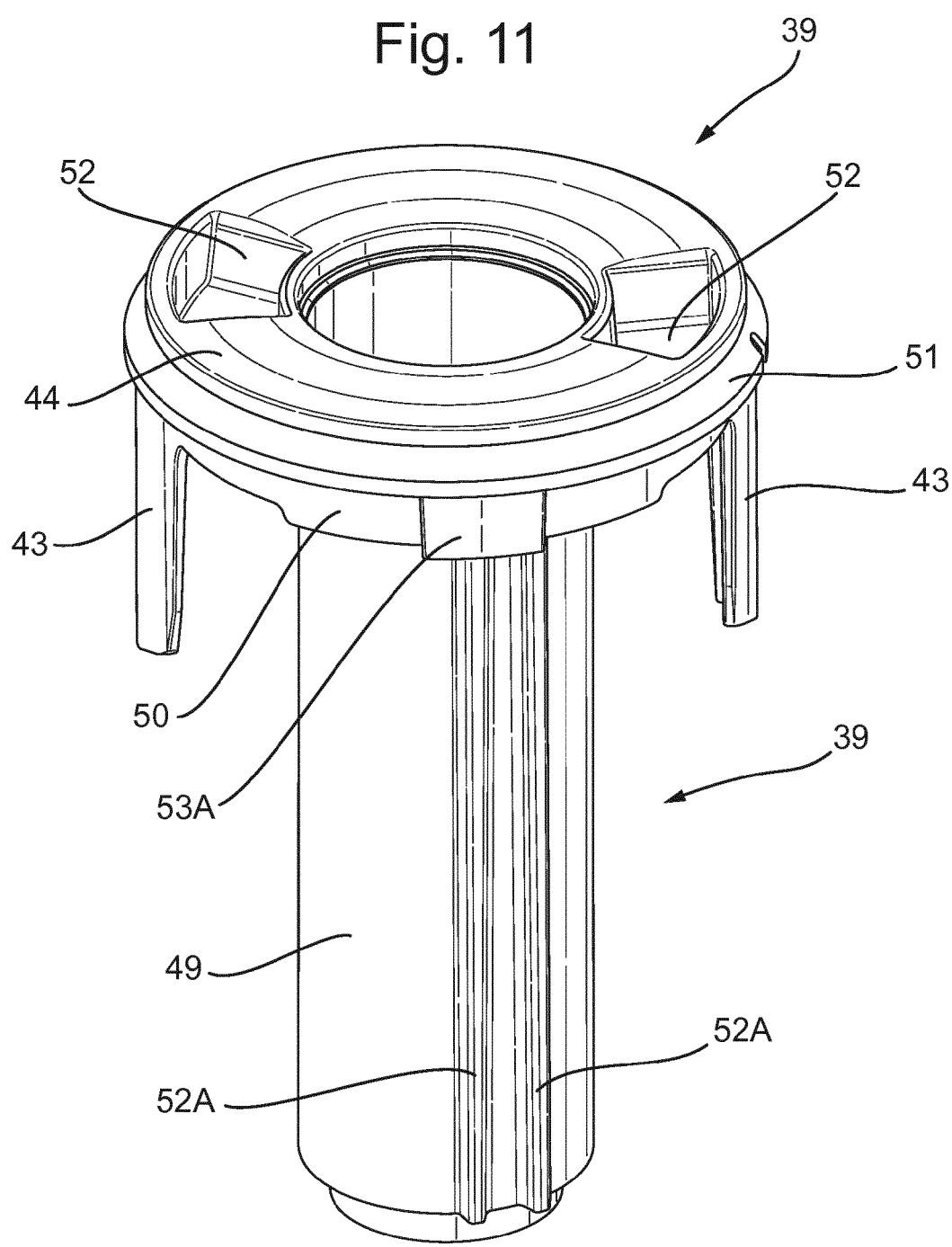
Figure 12:
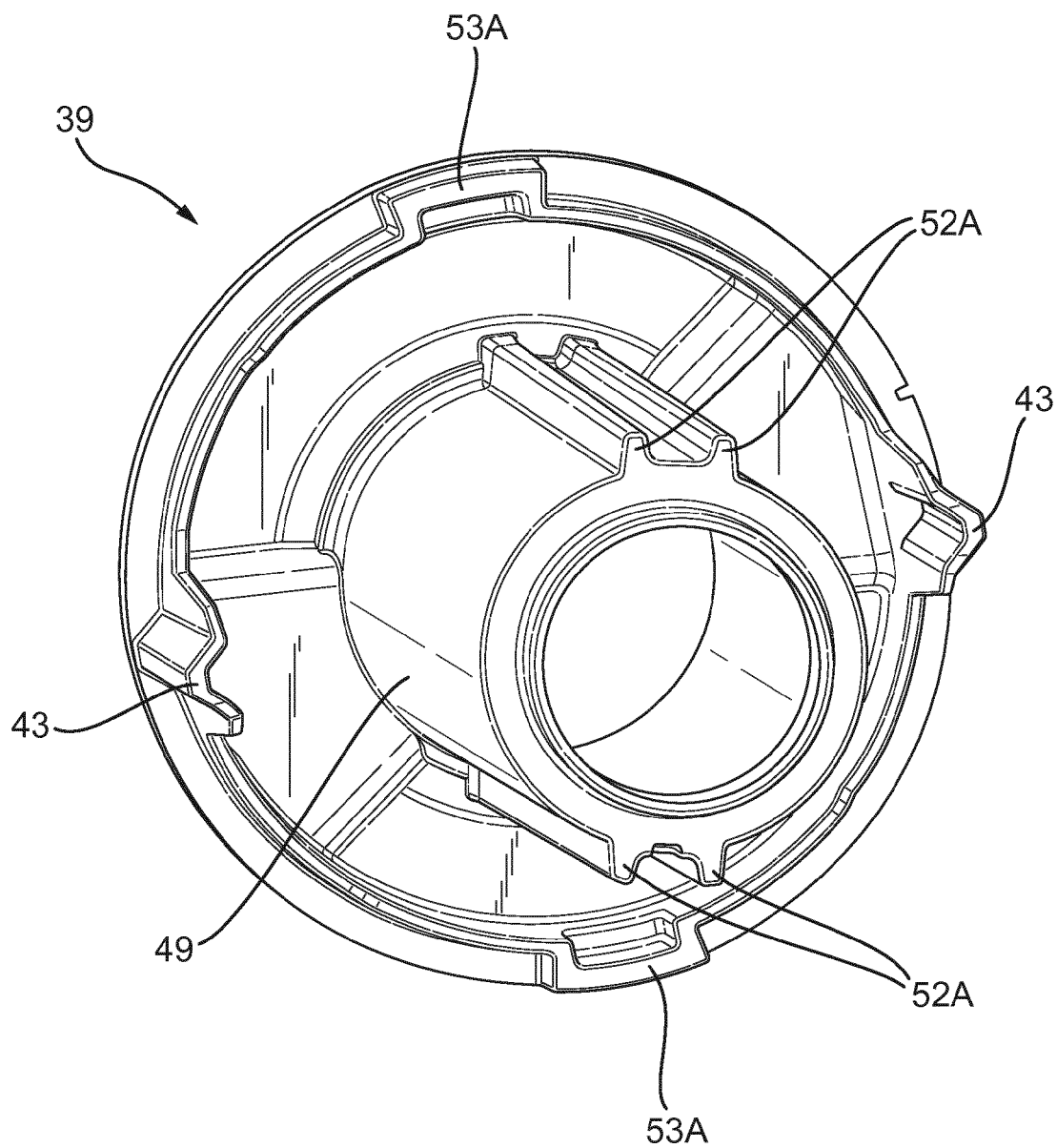
Figure 13:
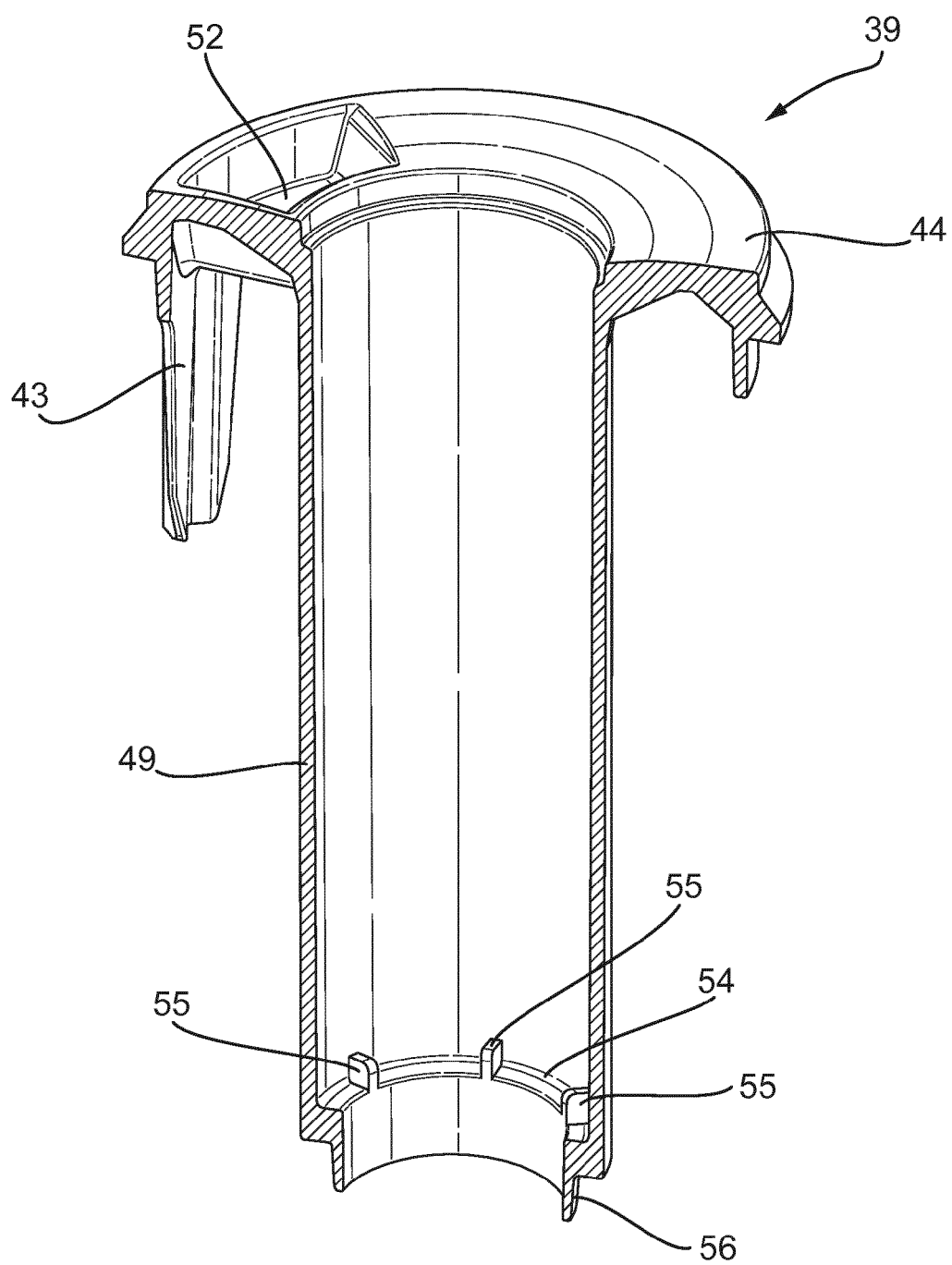

FIGS. 11, 12 and 13 are views of a refill holder (39) that is present within the cylindrical body (3). FIG. 11 is a view from a side and above; FIG. 12 is a view from below and FIG. 13 is a somewhat skewed lengthways cross-sectional view.

Figure 14:
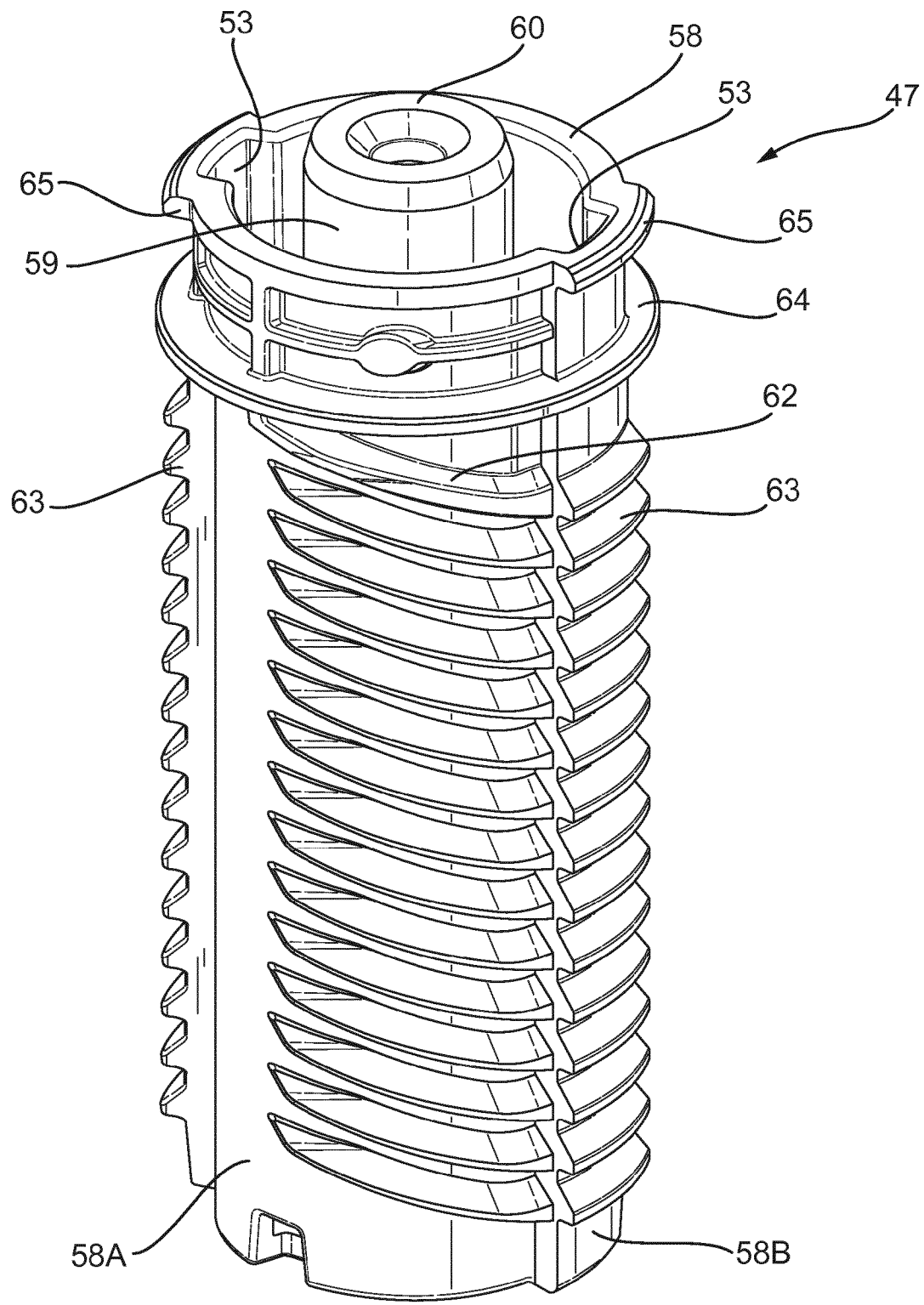
Figure 15:
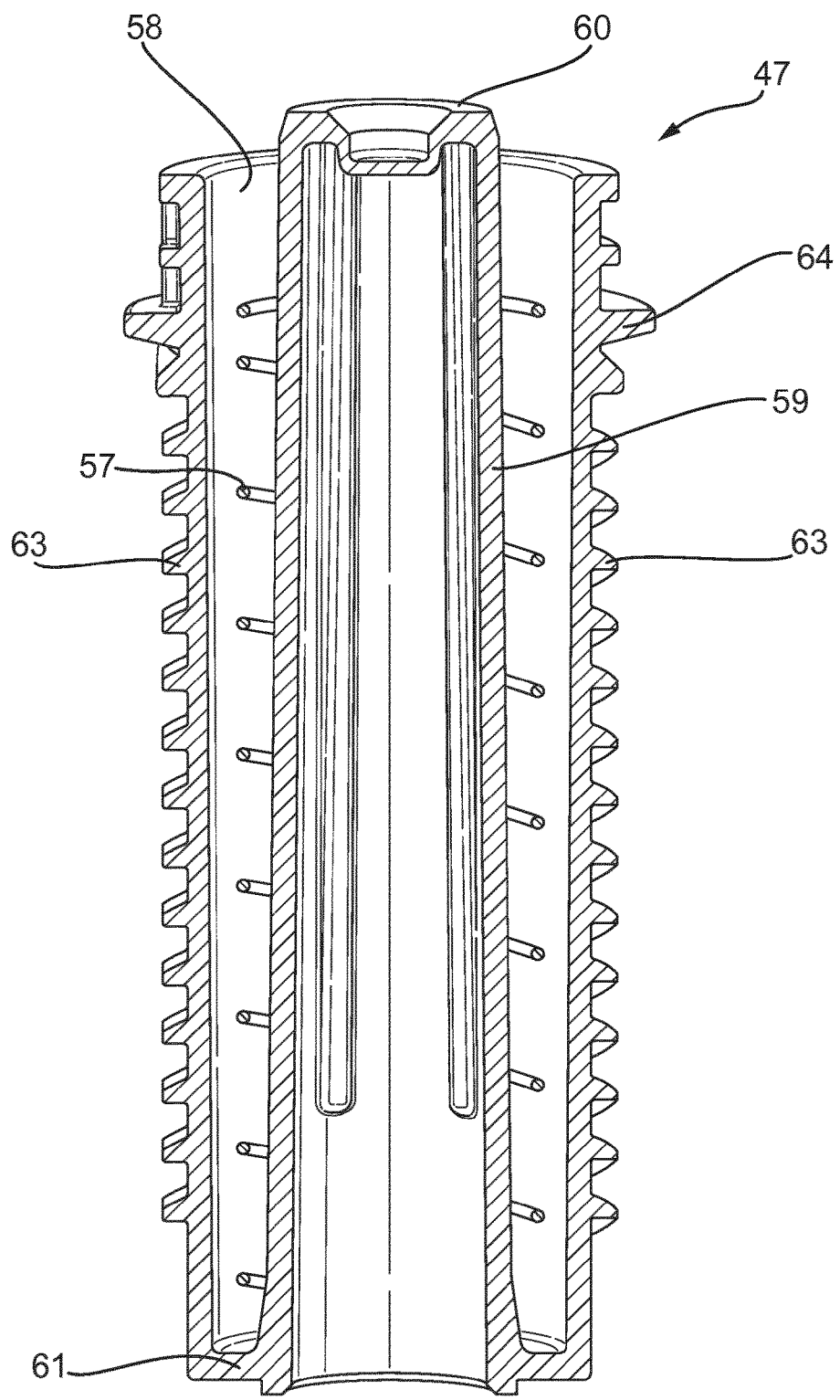

FIG. 14 is a view of a "plunger" (47) present within the cylindrical body (13) and FIG. 15 is a cross-sectional view of the same (from a different view point) and an associated reset spring (57).

Figure 16:
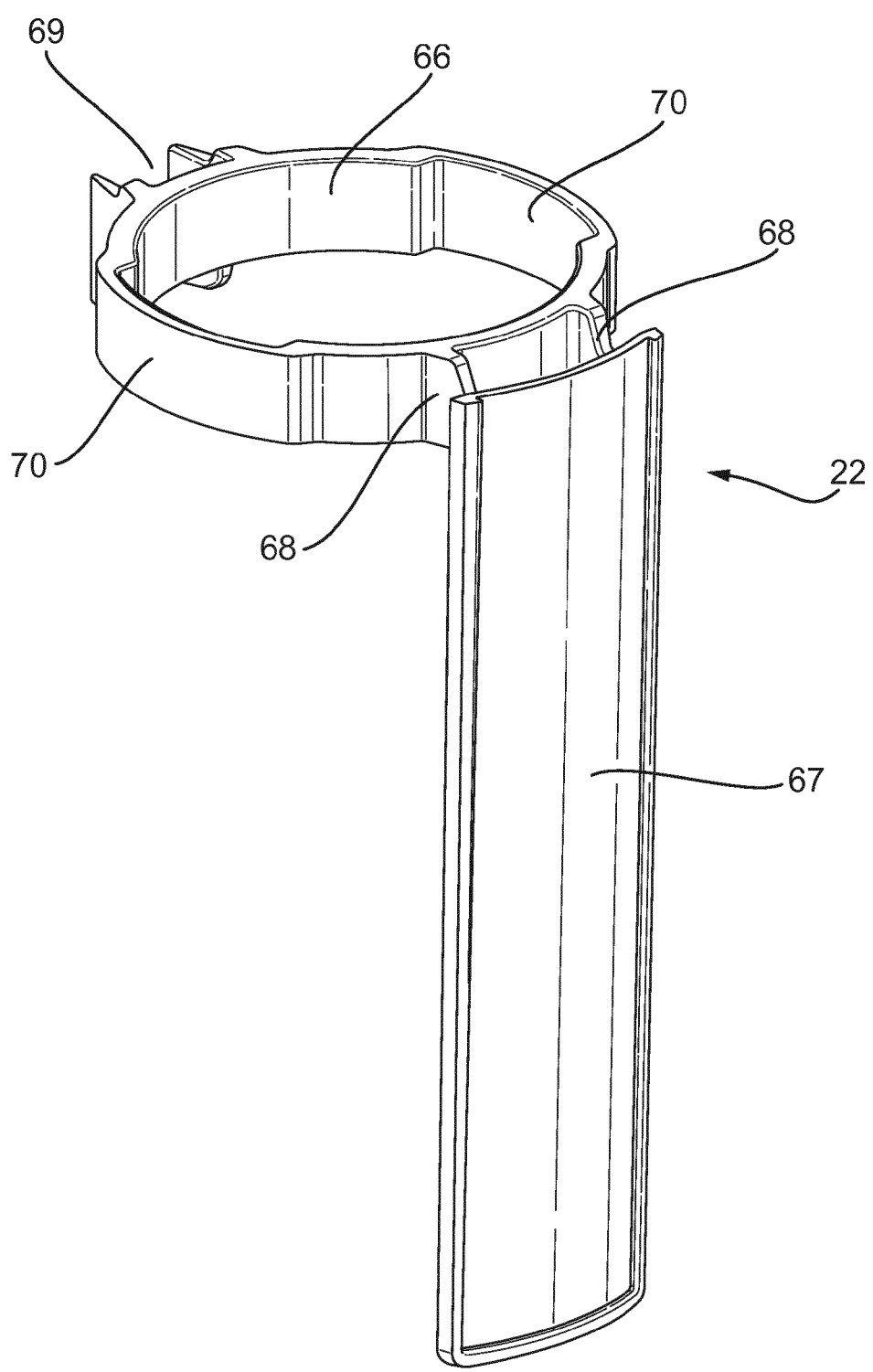

FIG. 16 is a view of a dose counter (22) used as part of the illustrated embodiment.

Figure 17:
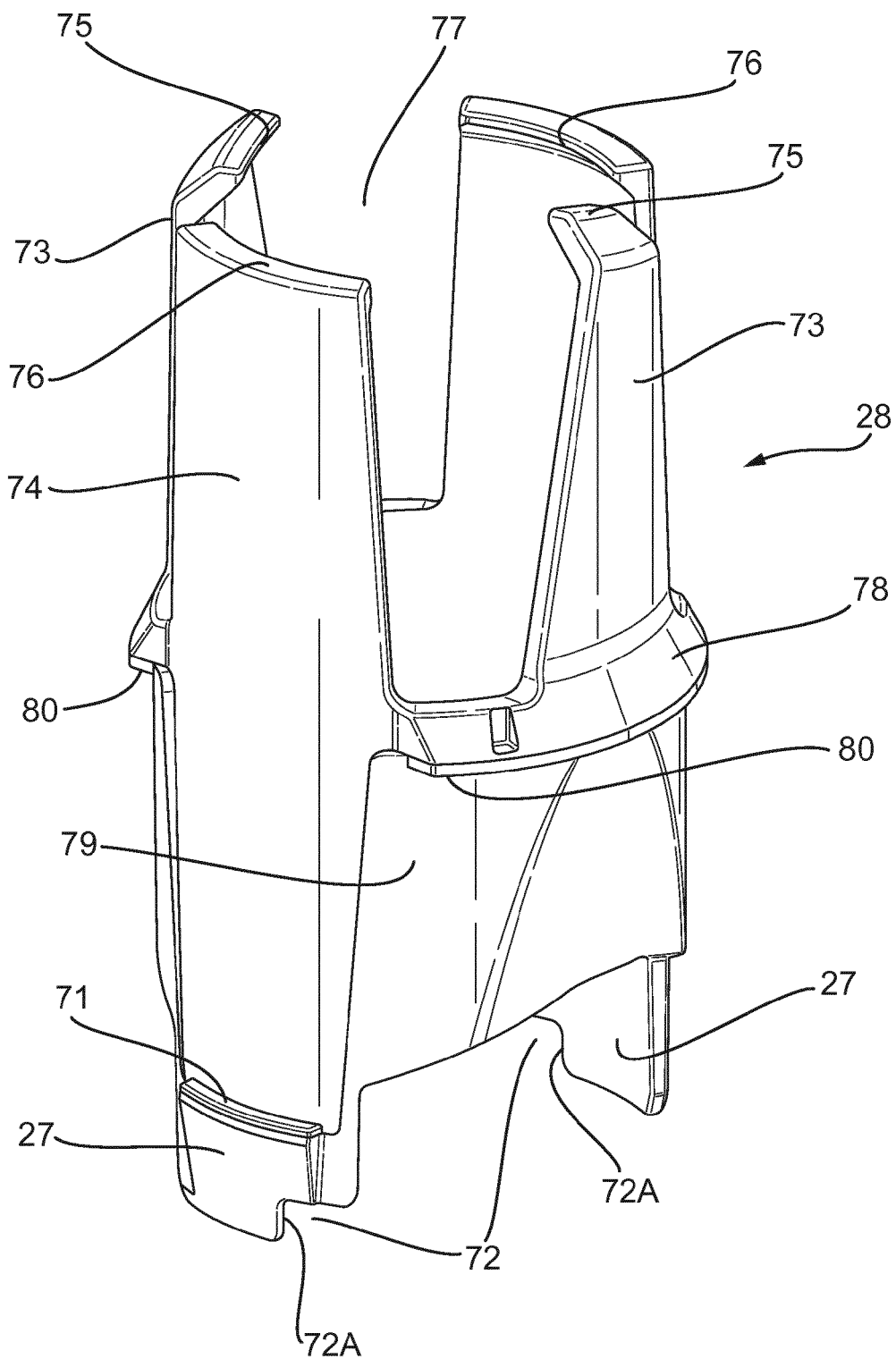

FIG. 17 is a view of a ratchet sleeve (28), used in conjunction with the plunger (47) and also held within the cylindrical body (13).

Figure 18:
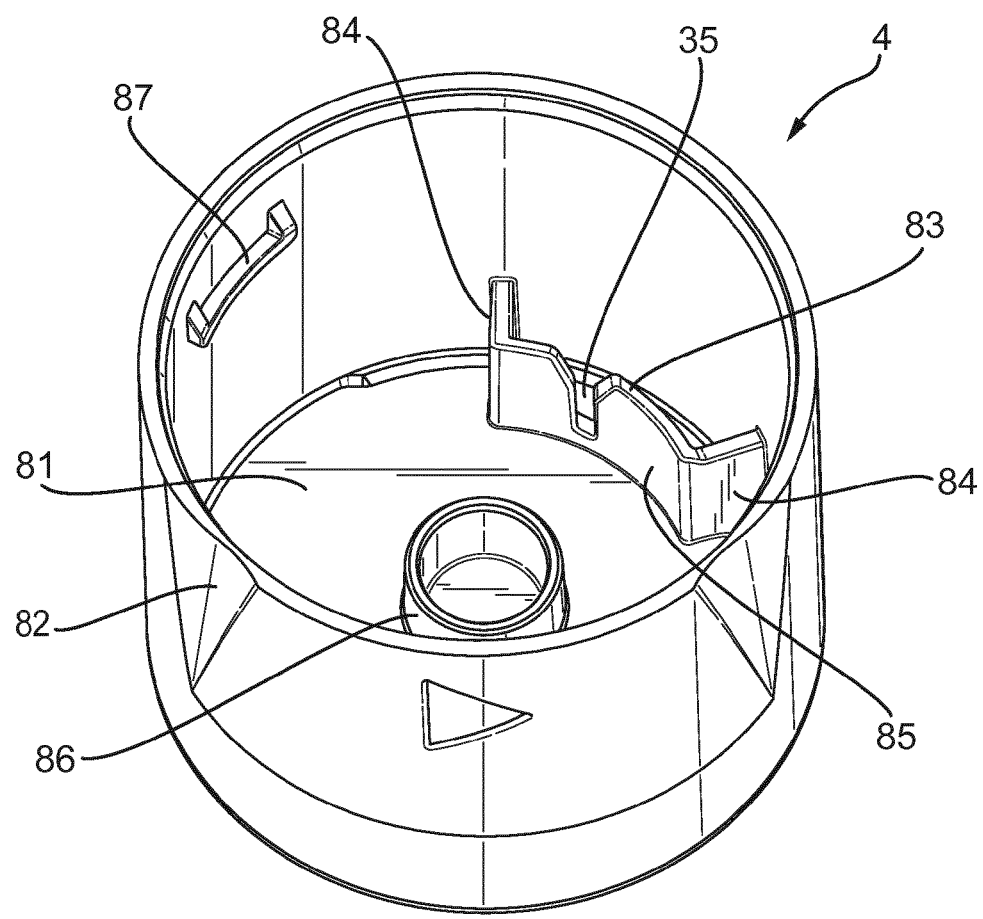

FIG. 18 is a view of dial unit (4) from the side and above.

Figure 19:
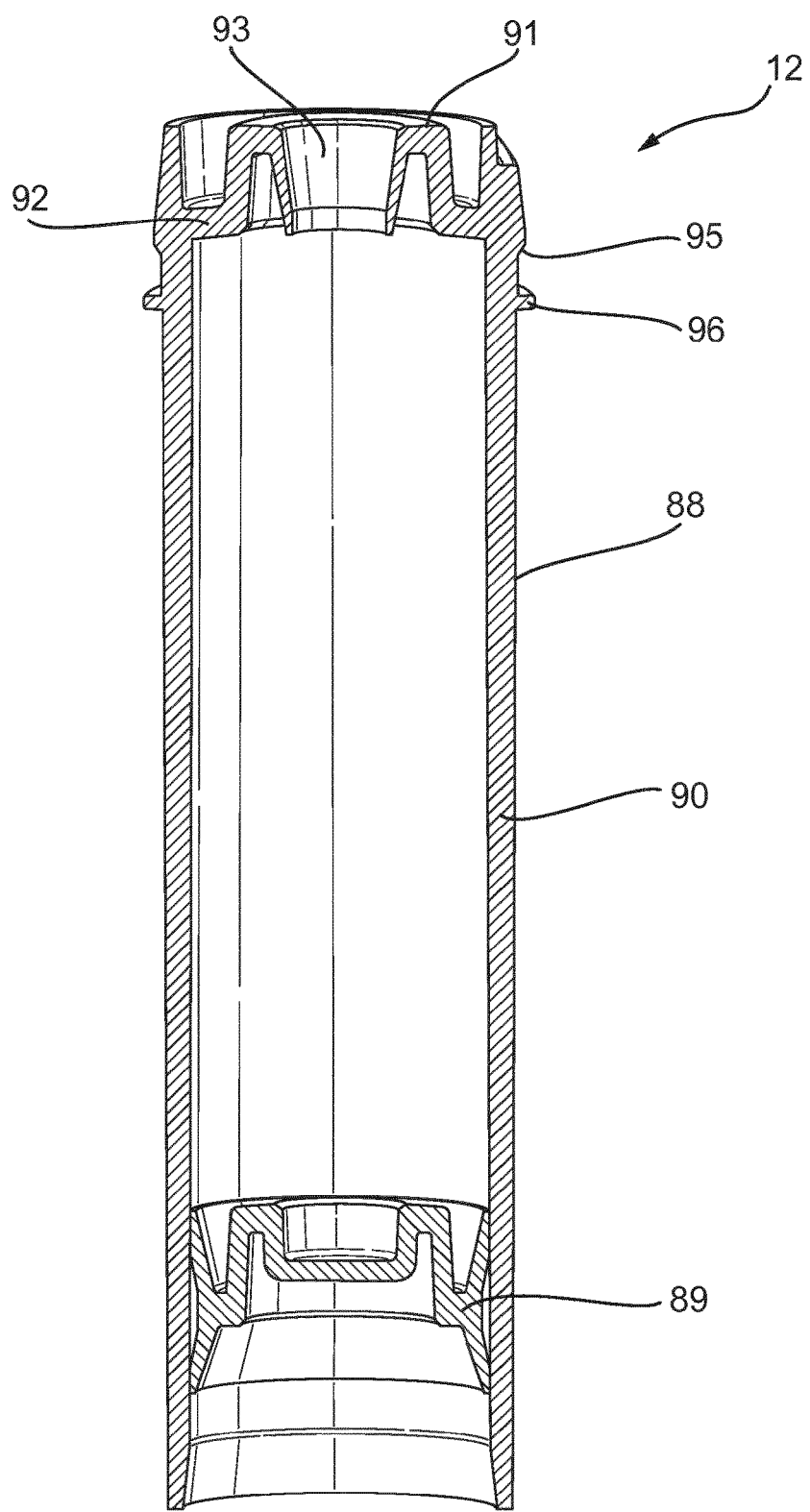

FIG. 19 is a cross-sectional view of a refill cartridge (12) used with the dispenser (1).

Figure 3:
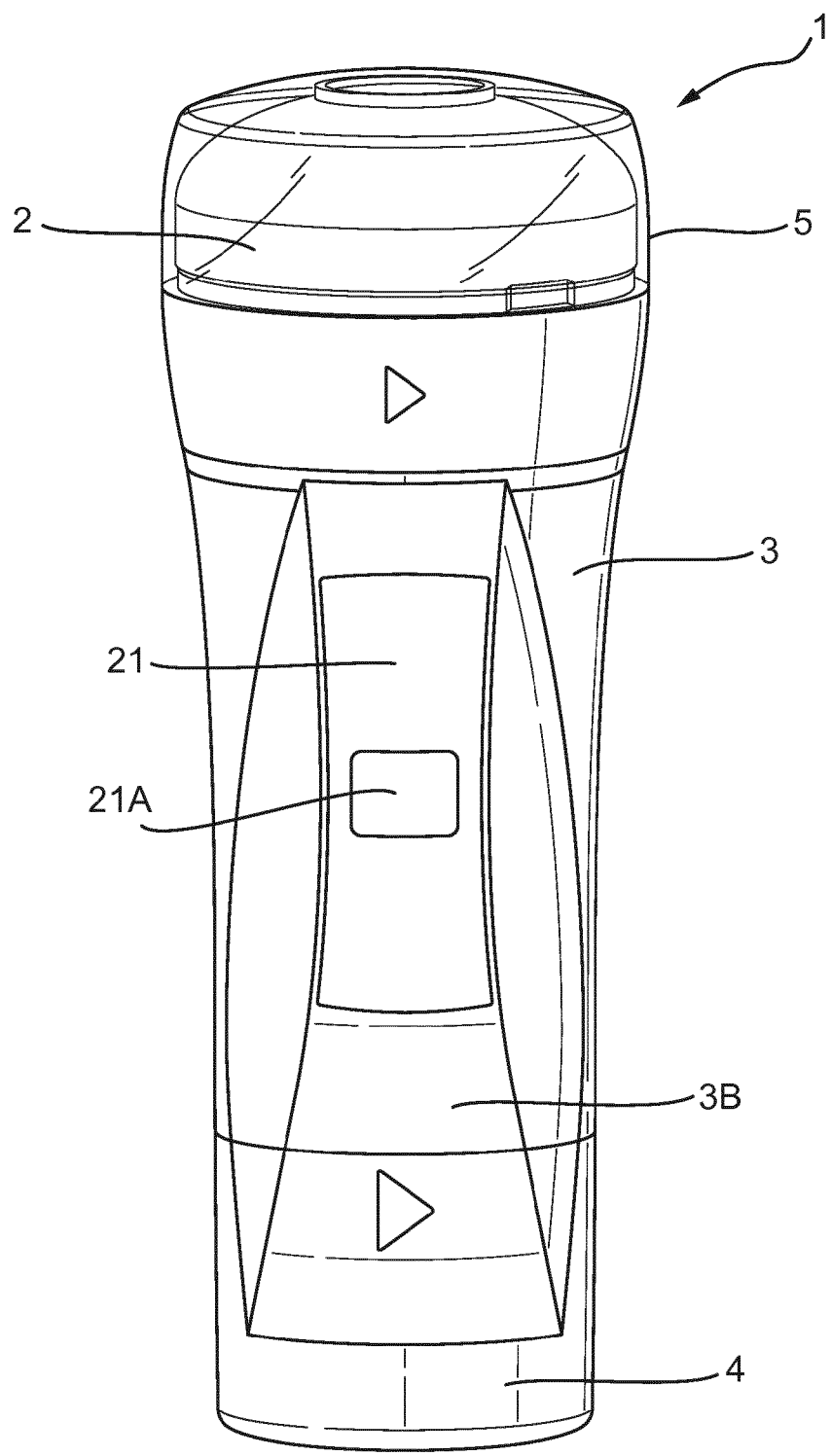
FIG. 3 is an exterior view from the front of the dispenser (1)
Figure 4:
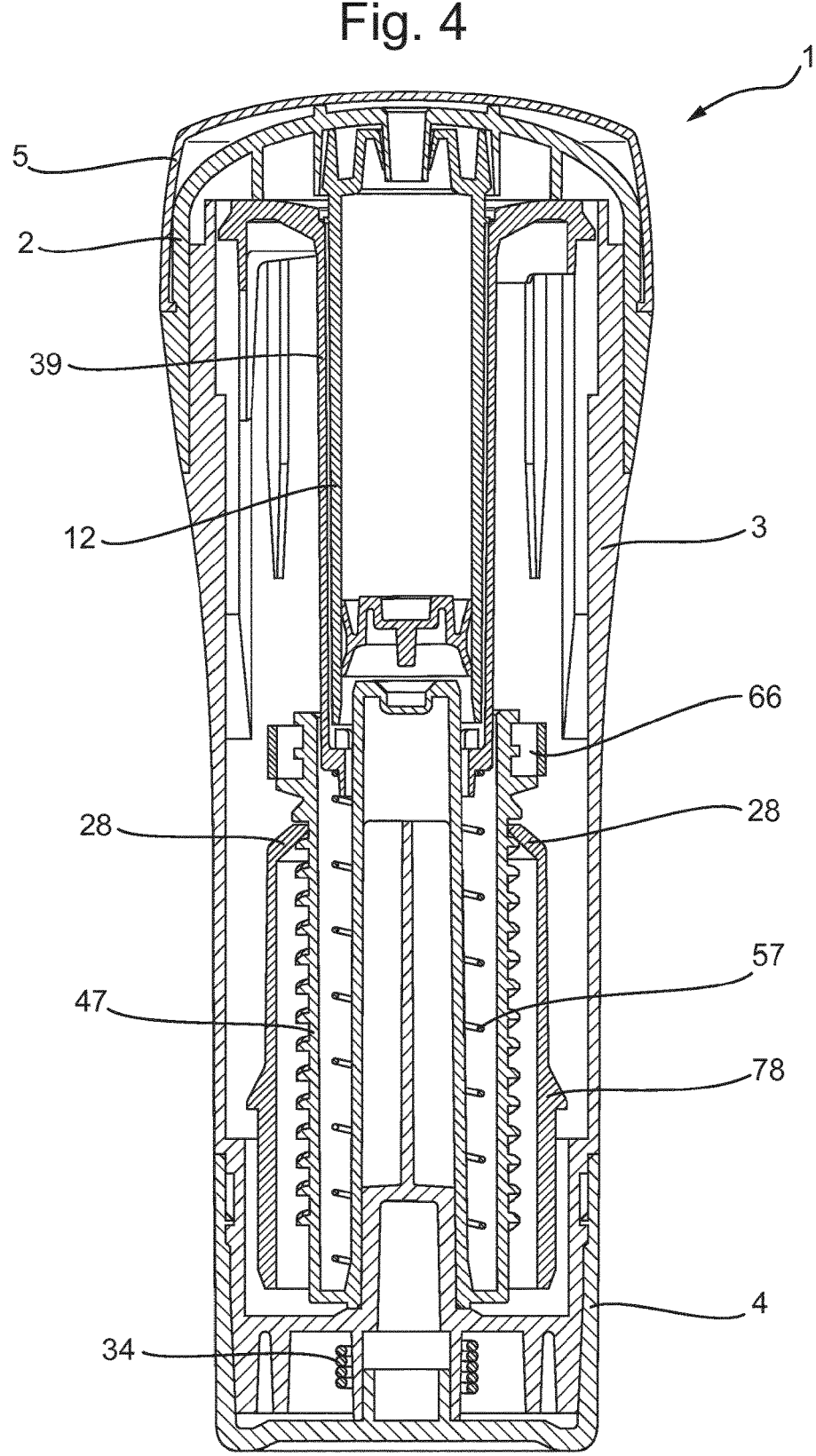
FIG. 4 is a lengthways cross-section through the dispenser (1), in its pre-actuated condition.

FIGS. 3 and 4 illustrate key components of the dispenser (1) and how they inter-relate. The dispenser (1) comprises an applicator head (2) attached to the upper end of a cylindrical body (3), which is in turn attached at its lower end to a dial unit (4). Within the cylindrical body (3), there are multiple components described further herein. On top of the applicator head (2) there is a removable over-cap (5), which can help reduce evaporative loss from a composition within a refill cartridge (12) used as part of the dispenser (1).

Figure 1:
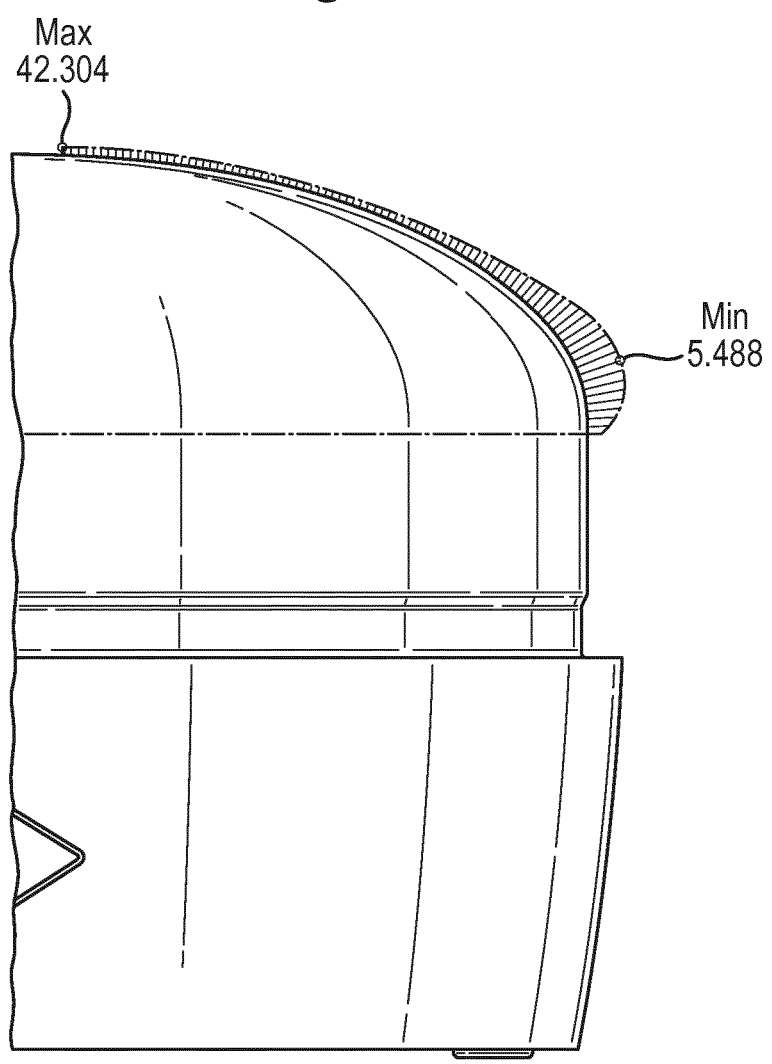
FIG. 1 illustrates the cross-sectional shape of the applicator head (2) with a curvature comb overlaid on the profile.
Figure 2:
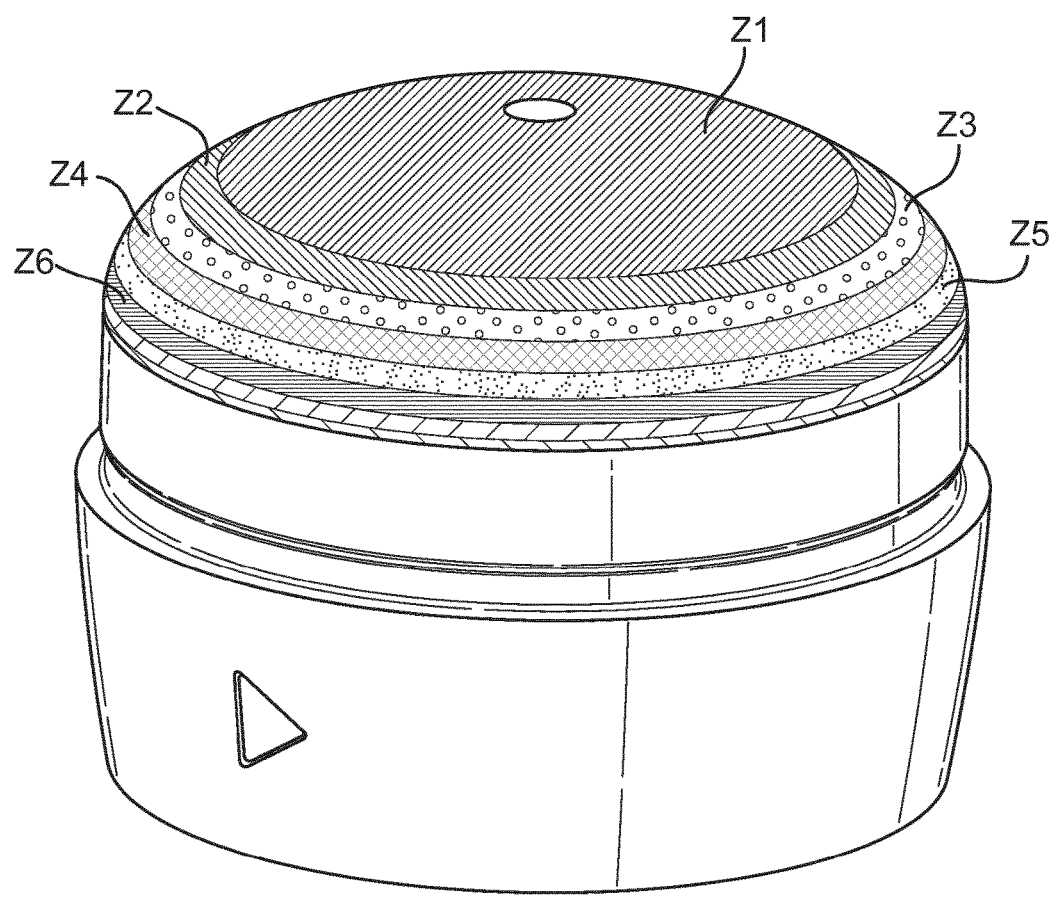
FIG. 2 illustrates the varying radii of curvature of the applicator head (2) as the distance from its top/centre increases.

The varying radii of curvature of the applicator head (2) are illustrated in FIGS. 1 and 2. FIG. 1 indicates that the applicator surface has a maximum radius of curvature of 42.304 mm at its top/centre and that this decreases to a minimum of 5.488 mm at its outer edge. The radius of curvature decreases at the same rate and to the same extent in whichever direction one travels outwards from its top/centre.

The curvature comb overlaid on the profile illustrated in FIG. 1 illustrates the curvature at different points on the dome profile. The length of each 'tooth' of the comb is an indication of the curvature at that point relative to the other points on the dome, the length of the tooth being inversely proportional to the radius of curvature.

FIG. 2 illustrates the varying radii of curvature of the domed-shaped surface of the applicator head (2). The radius of curvature decreases smoothly as the radial distance from the centre increases. Further, the rate of decrease of the radius of curvature (in degrees/mm) increases as the radial distance from the centre increases. The increasing radius of curvature as the dome-shaped surface merges into the vertical face of the cylindrical body (2) is not referenced.

It will be understood that the zones indicated on the surface of the applicator head (2) shown in FIG. 2 do not represent zones of equal radius of curvature, the radius of curvature changing suddenly when one passes from one zone to the next. Rather, there is a smooth decrease in the surface's radius of curvature as the radial distance from the centre increases. The zones illustrated, on going from the centre outwards, represent radii of curvature of:

From 42.3 down to 20.0 mm: Zone Z1;
From 20.0 down to 13.1 mm: Zone Z2;
From 13.1 down to 9.7 mm: Zone Z3;
From 9.7 down to 7.7 mm: Zone Z4;
From 7.7 down to 6.4 mm: Zone Z5; and
From 6.4 down to 5.5 mm: Zone Z6.

Figure 5:
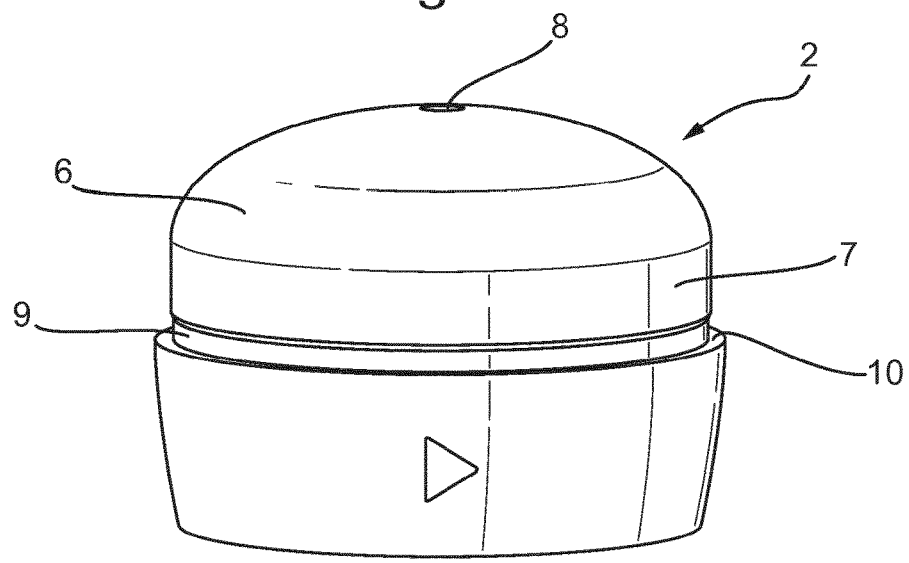
FIG. 5 is a view of the applicator head (2) of the dispenser (1) from the front.
Figure 6:
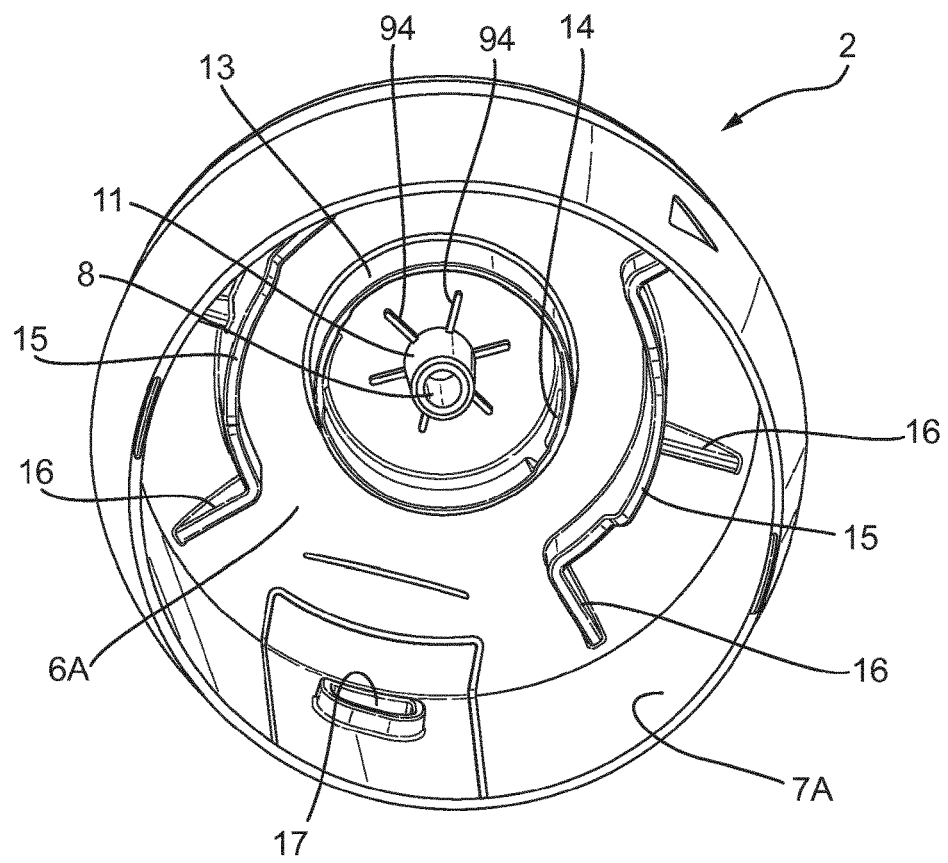
FIG. 6 is a somewhat skewed view of the applicator head (2) from below.

The applicator head (2) is further illustrated in FIGS. 5, 6 and 7. The applicator head (2) comprises a smooth convex upper outer surface (6) and a peripheral skirt (7) dependent therefrom. The upper surface (6) is pierced by a central aperture (8) through which the composition is propelled when the dispenser (1) is actuated.

The peripheral skirt (7) depends downwards with uniform external diameter for a distance, then, following an annular recess (9), there is an annular ledge (10) protruding radially outwards from the outer surface of the skirt (7). The width of the ledge (10) matches the thickness of the lower edge of the removable cap (5) designed to fit on top of the applicator head (2).

Moving downwards from the annular ledge (10), the external diameter of the peripheral skirt (7) narrows, until it is similar to that of the skirt (7) where it is above the annular recess (9). The internal diameter (i.d.) of the peripheral skirt (7) remains approximately constant for the full depth of the skirt (7), as illustrated in FIG. 7.

FIG. 6 illustrates that from around the central aperture (8), on the underside (6A) of the applicator head (2), there depends a cylindrical refill sealing projection (11). The refill sealing projection (11) serves to engage with a refill cartridge (12) for the dispenser (1) (vide infra).

From radially outside of the refill sealing projection (11), also on the underside (6A) of the applicator head (2), there depends a cylindrical refill retaining projection (13). From the inner surface of this projection (13), at its lower end, there protrude two diagonally opposed refill clips (14), which aid retention of the refill cartridge (12) in the refill retaining projection (13)(vide infra).

From radially outside of the refill retaining projection (13), also on the underside (6A) of the applicator head (2), there depend two diagonally opposed refill holder engagement tabs (15), together with various support walls (16). The refill holder engagement tabs (15) interact with the refill holder (39) and serve an important function when the refill cartridge (12) requires replacing (vide infra).

From the inner surface (7A) of the peripheral skirt (7), there protrude two diagonally opposed bayonet lugs (17) which serve to anchor the applicator head (2) to the cylindrical body (3), apart from when the refill unit (12) is being replaced (vide infra).

Cylindrical Body (3)

FIGS. 8, 9 and 10 illustrate features of the cylindrical body (3). These are described further in the following paragraphs.

At the upper end, on the outer surface of the cylindrical body (3), there is an applicator head sleeve (18), designed to hold the applicator head (2) via close contact with the internal surface (7A) of its peripheral skirt (7).

The applicator head sleeve (18) has a cut-away section (19) on its outer surface at its upper end. The cut-way section (19) continues into two diagonally opposed bayonet tracks (20) on the outer surface of the applicator head sleeve (18). These bayonet tracks (20) accept and hold the bayonet lugs (17) of the applicator head (2) when this is placed on top of the cylindrical body (3). The bayonet tracks (20) are designed to allow access of the bayonet lugs (17) when they are inserted from above, clockwise rotation of the applicator head (2) then locks the bayonet lugs (17) into the bayonet tracks (20) and prevents axial movement of the applicator head relative to the cylindrical body (3). When the applicator head (2) needs to be removed (typically when the refill unit requires replacing), the applicator head (2) is rotated counter-clockwise and the bayonet lugs (17) of the applicator head (3) may then be lifted clear of the bayonet tracks (20) of the cylindrical body (3).

To the centre of the front of the cylindrical body (3), and illustrated only in FIG. 3, there is affixed a control panel plate (21). The control panel plate (21) defines a dose window (21A), through which the reading on a dose counter (22) (vide infra) may be observed. The dose counter (22) sits within a dose counter cut-away (23) defined by the inner wall (3A) of the cylindrical body (3).

The dose counter (22) sits largely behind the aforementioned control panel plate (21), although it does protrude significantly below said plate (21), when the refill cartridge (12) of the dispenser (1) is full.

The dose counter cut-away (23) comprises gaps through the full depth of the cylindrical body (3) in a segment (23A) at the front of the cylindrical body (3) within the bounds of the control panel plate (21) and in segment (23B) below the control panel plate (21); the two segments (23A and 23B) are separated by a thickened section (3B) at the front of cylindrical body (3).

A further feature of the cylindrical body (3) protruding radially from its outer surface towards its bottom, is a dial sleeve rib (24), which is in large part responsible for axially anchoring the dial unit (4) to the base of the cylindrical body (3).

Towards the base of the cylindrical body (3), there are two diagonally opposed radial recesses (25) which function as rotation channels for engagement pockets (83) holding retention blades (27) of a ratchet sleeve (28) (vide infra). Each rotation channel (25) is bounded at its clockwise radial face by a "set stop face" (29) and at its counter-clockwise radial face by an "end-of-dose stop face" (30). These stop faces (29) and (30) interact with corresponding faces on the dial unit (4) to limit relative rotation thereof.

The back walls of the aforementioned "radial recesses" form part of a cylindrical wall (31) depending from the edge of a central inner horizontal platform (32) towards the base of the cylindrical body (3). A horizontal gap exists between the edge of the central inner horizontal platform (32) and the outer wall (3C) of the cylindrical body (3) where the rotational channels (25) are defined. This gap allows essential linkage between the dial unit (4) and the ratchet sleeve (28).

Within the cylindrical wall (31) and also depending from the inner platform (32), there is an inner cylindrical wall (33). The inner cylindrical wall (33) depends downwards slightly further than the "outer" cylindrical wall (31), i.e., it has slightly greater depth. This has implication with regard to the axially binding the dial unit (4) to the cylindrical body (vide infra).

FIG. 10 illustrates that around the inner cylindrical wall (33) there is wound a dial spring (34). The dial spring (34) is a torsion spring and provides a clockwise rotational restoring force between the dial unit (4) and the cylindrical body (3). The lower end of the dial spring (34) is held by a dial spring retaining channel (35) in the dial unit (4), with which it may be rotated. The upper end of dial spring (34) is fixedly held against a dial spring reaction face (36) on the bottom of the cylindrical body (3).

One section of the aforementioned (outer) cylindrical wall (31), where it is part of a rotation channel (25), defines a dial spring cut-away (37) for the dial spring (34). This part of the cylindrical wall (31) is of lesser depth, enabling the lower end of the dial spring (34) to pass below it and rotate in counter-clockwise direction as the dial unit (4) is so turned by rotational force, and then to rotate back to its starting position when the resulting rotational tensioning of the spring is released.

Features on the inner wall (3A) of the cylindrical body (3) are best illustrated in FIG. 9. Protruding from the top inner edge are four refill holder clips (38) which serve to retain a refill holder (39) for replaceable refill cartridges (12) used as part of the present embodiment. Also assisting in the retention of the refill holder (39) are four ledges (38A) that protrude outwards from the inner wall (3A) of the cylindrical body (3) a short distance below the refill holder clips (38).

The inner wall (3A) of the cylindrical body (3) defines restraining features for other components of the dispenser (1). Thus, there are two diagonally opposed recesses towards the top of said inner wall (3A) that function as rotation limit pockets (40) for the refill holder (39), i.e., they constrain the rotation of the refill holder (39) relative to the cylindrical body (3). These rotation limit pockets (40) are located above the dose counter cut-away (23) and a dose counter anti-rotation spline (41) diagonally opposed thereto.

The inner wall (3A) of the cylindrical body (3) defines two diagonally opposed recesses towards the top of said inner wall (3A) that function as "detent pockets" (42). These detent pockets (42) are located on a diagonal orthogonal to that bearing the rotation limit pockets (40). The detent pockets (42) serve to accommodate detent arms (43) protruding downwards from a collar (44) at the top of the refill holder (39). At their radial centres, each detent pocket (42) has a vertically orientated rib (42A) protruding slightly outwards (vide infra).

Towards its bottom, and running completely around the inner wall (3A) of the cylindrical body (3), there is a narrow, inwardly projecting radial shelf (45), which serves as an axial bearing for the ratchet sleeve (28).

Projecting upwards from the centre of the central inner horizontal platform (32) of the cylindrical body (3) there is a centralising boss (46) for a plunger (47) (vide infra). The centralising boss (46) is cylindrical at it base but has cross-shaped cross-section for most its length.

Within or partially within the cylindrical body (3) there are other key components of the dispenser (1) described further herein. Such key components include a refill holder (39), which holds the refill cartridge (12) for the dispenser (1); a "plunger" (47), which serves to force a fluid product from the refill cartridge (12) and a "ratchet sleeve" (28) which forces the plunger (47) upwards when the dial unit (4) is turned counter-clockwise with respect to the cylindrical body (3).

The refill holder (39) is illustrated in FIGS. 4, 11, 12 and 13. The refill holder (39) comprises a cylindrical body (49) and an annular collar (44) expanding horizontally from the upper edge thereof. The cylindrical body (49) of the refill holder (39) is hollow at its centre and the hollow is designed to accommodate the refill cartridge (12) for use with the dispenser (1).

The collar (44) expanding radially from the upper edge of the cylindrical body (49) of the refill holder (39) comprises a downward depending annular sleeve (50) at its outer circumference. The annular sleeve (50) has an outward sloping annular eave (51). This serves to axially retain the refill holder (39) within the cylindrical body (3) of the dispenser (1), the annular eave (51) fitting between the refill holder clips (38) and the ledges (38A) protruding from the inner wall (3A) of the cylindrical body (3).

Protruding downwards from the annular sleeve (50) are two diagonally opposed detent arms (43) which engage with the detent pockets (42) in the inner wall (3A) the cylindrical body (3). The detent arms (43) have an outwardly pointing truncated-V cross-section. The radially outer ends of the detent arms (43) and the vertically orientated ribs (42A) in the centre of the detent pockets (42) of the cylindrical body (3) provide resistance to the free rotation of the one relative to the other. When the refill holder (39) is rotated [by rotation of the applicator head (2)], the detent arms (43) are forced over the ribs (42A) protruding from the detent pockets (43) of the cylindrical body (3), providing a resistance to said rotation.

The top surface of the circular collar (44) defines two diagonally opposed engagement pockets (52) for holding engagement tabs (15) of the applicator head (2). The engagement pockets (52) are inset into the circular collar (44) at radial positions adjacent to where the detent arms (43) depend from the circular collar (44). The interaction of the engagement tabs (15) of the applicator head (2) with the engagement pockets (52) of the refill holder (39) provides a rotational lock between these components.

Running down the outer surface of the cylindrical body (49) of the refill holder (39) are two sets of diagonally opposed "plunger splines" (52A). These splines (52A) interact with recesses (53) in the plunger (47) described in detail below and rotationally lock the plunger (47) to the refill holder (39), without hindering the relative axial movement of the two which is essential to the functioning of the dispenser (1).

Projecting radially outwards from the annular sleeve (50) are two diagonally opposed bosses (53A). These bosses (53A) exist on a diagonal orthogonal to that bearing the detent arms (43) and the engagement pockets (52). The bosses (53A) limit the rotation of the refill holder (39) relative to the cylindrical body (3) by interaction with the rotation limiting pockets (40) thereof (vide supra).

The rotational limits of the bosses (53A) of the refill holder (39) within the rotation limiting pockets (40) of the cylindrical body (3) define the limits rotation of the detent arms (43) within the detent pockets (42) of the cylindrical body (3). Further, the rotational limits of these sets of features correspond to those of the rotation of the bayonet lugs (17) of the applicator head (2) within the bayonet tracks (20) incised into the outer surface of the cylindrical body (3).

FIG. 13 illustrates that close to the bottom of the cylindrical body (49) of the refill holder (39), there is an inwardly projecting radial shelf (54). Sat on top of this radial shelf (54) at regular angular intervals are six refill stop splines (55) which serve as axial bearings for the bottom of the refill cartridge (12).

Below the radial shelf (54), the outer surface of the cylindrical body (49) has a recessed section (56) of reduced inner and outer diameter. This section (56) of the cylindrical body (49) serves as a retaining boss for an optional compression spring (57) that acts between the refill holder (39) and the plunger (47) as a reset spring, biasing the plunger (47) downwards.

Within the cylindrical body (3) there is a plunger (47). This illustrated in FIGS. 4, 14 and 15.

FIG. 15 is a cross-section also illustrating the relative position of the reset spring (57).

The plunger (47) comprises an outer cylindrical shell (58) surrounding an inner cylindrical boss (59) which is hollow along its central axis. The cylindrical boss (59) is topped by a drive face (60) which protrudes somewhat above the surrounding outer cylindrical shell (58). The inner cylindrical boss (59) and outer cylindrical shell (58) share a common axis and are linked at their base by a reset stop face (61). The bottom of the inner cylindrical boss (59), within the reset stop face (61), is open, allowing access for the centralising boss (46) of the cylindrical body (3).

The outer cylindrical shell (58) comprises two types of teeth on its outer surface: advancing helix teeth (62) and non-return horizontal teeth (63).

There are two sets of non-return horizontal teeth (63) diagonally opposed on the outer surface of outer cylindrical shell (58) and each extends for an angular distance of about 40°.

The non-return teeth (63) are of triangular cross-section and each tooth is in a plane orthogonal to the central axis, i.e. in a horizontal plane, and each set comprises teeth stacked equidistantly one above another.

There are also two sets of advancing helix teeth (62) diagonally opposed on the outer surface of outer cylindrical shell (58). These teeth are of greater radial extent than the non-return teeth (63), each extending for an angular distance of about 80°.

The advancing helix teeth (62) are of triangular cross-section and slope helically downwards in a counter-clockwise direction around the outer surface. Each set of advancing helical teeth (62) comprises teeth stacked equidistantly one above another.

The non-return teeth (63) and the advancing helix teeth (62) are of (approximately) the same cross-sectional radial height and are of similar shape for much of the length of the advancing helix teeth (62), although the latter do slope into the surface from which they protrude at their clockwise end.

The non-return teeth (63) and the advancing helix teeth (62) are of (approximately) equal vertical spacing.

Each set of the advancing teeth (62) protrude from a section (58A) of the outer cylindrical shell (58) recessed relative to raised sections (58B) of the outer cylindrical shell (58), from which the non-return teeth (63) protrude.

The recessed sections (58A) are recessed such that the outer pinnacle of each of the advancing teeth (62) protrudes to a radial extent equal to or below the troughs between the non-return teeth (63).

Each advancing helix tooth (62) rises from its recessed section (58A) of the outer cylindrical shell (58) at its most clockwise point and slopes helically downward in a counter-clockwise direction. The downward slope is such that the pinnacle of an advancing tooth (62) drops a distance approximately equal to that between adjacent advancing helix teeth (62), which is in turn approximately equal to that between adjacent non-return teeth (63), between its most clockwise point and its most counter-clockwise-point.

From the clockwise edge of each set of advancing helix teeth (62), the recessed sections (58A) from which said teeth protrude extend smoothly for a further radial distance of about 45° clockwise to the next raised section from which non-return teeth (63) protrude. By "smoothly" it is to be understood that there are no teeth (62 or 63) in this region specified, although other annular raised features do cut across it at its upper end (vide infra).

The raised sections (58B) of the outer cylindrical shell (58) are radially extended relative to the recessed sections (58A), with which they share a common central axis for their radii of curvature.

The plunger (47) comprises, at close to its upper end, features to retain the dose counter (DC) (22) (vide infra). These features are a DC retaining shelf (64) and above that two DC retaining clips (65), both extending radially from the outer surface of its outer cylindrical shell. The former (64) is a full annular protrusion, whilst the latter (65) only protrude at diagonally opposed sections which radially overlap the segment (58B) of the outer cylindrical shell (58) bearing the non-return teeth (63).

The inner surface of the outer cylindrical shell (58) of the plunger (47) defines two diagonally opposed recesses (53) extending the full length thereof. These recesses (53) accommodate the plunger splines (52A) of the refill holder (39), rotationally locking these two components together.

The dose counter (22) is illustrated in FIG. 16. It comprises a retaining hoop (66) in the form of an annular ring and a "flag" (67) attached thereto by an outwardly projecting flag retaining projections (68). The flag (67) extends down a side of the cylindrical body (3) in linear fashion and is curved inwards in a horizontal plane along its length, sharing a common axis with the cylindrical body (3), to ease its fitting within said cylindrical body (3). The flag (67) has an angular extent of approximately 50°.

The retaining hoop (66) of the dose counter (22) is held between the DC retaining shelf (64) and the DC retaining clips (65) of the plunger (47). In this way, the dose counter (22) is forced upwards whenever the plunger (47) is forced upwards. Numbers (not illustrated) on the outer surface of the dose counter flag (67) may be used to indicate doses delivered or doses remaining. Such numbers may be seen through the dose window (21A) present in the control panel plate (21).

The retaining hoop (66) has a rear lug (69) diagonally opposite the flag retaining projections (68). The rear lug (69) comprises two radial projections that fit into the DC anti-rotation spline (41) cut into the inner wall (3A) of the cylindrical body (3) and extending for the upper half thereof. This maintains the flag (67) in correct rotational orientation with respect to the cylindrical body (3) at all times.

At right angles to the rear lug (69) and the flag retaining projections (68), the retaining hoop (66) has diagonally opposed plunger recess clips (70). These radially expanded sections of the retaining hoop (66) allow passage of the retaining hoop (66) over the DC retaining clips (65) when the dose counter (22) is being fitted to the plunger (47). [During assembly (vide infra) the dose counter (22) is rotated after the plunger recess clips (70) are pushed over the DC retaining clips (65) in order to fix it axially in place on the plunger (47)].

The ratchet sleeve (28) is illustrated in FIGS. 4 and 17. It is of overall tubular construction and fits around the plunger (47) largely within the cylindrical body (3).

At the base (or bottom) of the ratchet sleeve (28) there are two diagonally opposed retention blades (27) that protrude downwards from the base of the ratchet sleeve (28) and interact with engagement pockets (83) in the dial unit (4) (vide infra). This interaction rotationally locks the ratchet sleeve (28) to the dial unit (4).

The retention blades (27) of the ratchet sleeve (28) each have retaining clips (71) on their upper outer surfaces. When assembled, the retaining clips (71) engage under lower edges (25A) of the cylindrical body (3) created by the two diagonally opposed radial recesses which function as rotation channels (25) for the engagement pockets (83) of the dial unit (4) (see FIG. 8).

The retention blades (27) of the ratchet sleeve (28) each define a cut-away section (72) at their lower counter-clockwise corners. The vertical face of one of these serves as a stop face (72A) for the lower end of the dial spring (34), together with the dial spring retaining channel (35) of the dial unit (4) mentioned above.

The upper part of the ratchet sleeve (28) comprises two sets of ratchet blades (73 and 74), each set protruding upwards from approximately half way up the ratchet sleeve (28) and each blade being diagonally opposed to its counterpart. The first set of ratchet blades (73) bear advancing ratchets (75) sloping inwards at their upper ends. The advancing ratchets (75) interact with the advancing helix teeth (62) of the plunger (47) (vide supra) and serve to drive the plunger (74) upwards when the ratchet sleeve (28) turns counter-clockwise. The second set of ratchet blades (74) bear non-return ratchets (76) projecting radially inwards from their upper ends. The non-return ratchets (76) interact with the non-return teeth (63) of the plunger (47) and serve to prevent downward return of the plunger (47) when an advancement is completed and the dial spring (34) forces the dial unit (4) and associated ratchet sleeve (28) to rotate clockwise back to the "set" position (vide infra).

The advancing ratchets (75) extend inward the farther, in order to interact with the advancing teeth (62) on the plunger (47), which are recessed relative to the non-return teeth (63).

The advancing ratchets (75) slope (vertically) downwards in a counter-clockwise direction, their slope matching that of the advancing teeth (62) on the plunger (47).

The non-return ratchets (76) are horizontal, like the non-return teeth (63) on the plunger with which they interact.

At the top end of the blade bearing them, the advancing ratchets (75) extend for approximately 30° and are diagonally opposed.

At the top end of ratchet bearing them, the non-return ratchets (76) extend for approximately 60° and are diagonally opposed.

The top ends of the ratchet blades (73 and 74) define circumferential gaps (77) in the ratchet sleeve (28). Each ratchet blade bearing the advancing ratchets (75) is separated, at its top end, from its neighbouring ratchet blades bearing the non-return ratchets (76) by an angular gap of approximately 60° in a clockwise direction and by an angular gap of approximately 30° in a counter-clockwise direction.

The circumferential gaps in the ratchet sleeve (28), defined by the ratchet blades (73), extend downwards for approximately half the length (height) of the ratchet sleeve (28).

The ratchet blades (73) bearing the advancing ratchets (75) expand, in a non-symmetrical fashion, as they progress downwards, each covering an angular extent of approximately 60° at their base, where they join a shelf (78) that slopes outwards from a full cylindrical part (79) of the ratchet sleeve (28) below. The blades (73) expand downwards in linear fashion, with most of the expansion occurring on the clockwise edges. The outwardly sloping shelf (78) extends horizontally around the full base of said ratchet blades (73) and extends as far as the nearest edges of the neighbouring ratchet blades (73) bearing the non-return ratchets (76).

The ratchet blades (73) bearing the non-return ratchets (76) each expand, in a symmetrical linear fashion, as they progress downwards, each covering an angular extent of approximately 66° at their base, where they merge with the full cylindrical part of the ratchet sleeve (28).

The shelves (78) at the bases of the ratchet blades (73) bearing the advancing ratchets (75) slope radially outward and downward and create horizontal thrust bearing faces (80) beneath them where they overhang the full cylindrical part of the ratchet sleeve (28). These thrust bearing faces (80) sit on axial bearings (45) within the cylindrical body (3) (vide supra).

At the base of the cylindrical body (3) is the dial unit (4). This is illustrated in FIGS. 3, 4, and 18. This is a cup-shaped unit having a largely flat solid circular base (81) and an outer solid cylindrical wall (82) rising from the outer edge of said base (81). Internally, on the base (81) of the dial unit (4) there are two diagonally opposed engagement pockets (83), each comprising two short walls (84) projecting radially inward from the cylindrical wall (82) across the circular base (81) linked by a curved inner wall (85), also extending across the circular base (81), sharing the same plane of curvature as the outer cylindrical wall (82). The engagement pockets (83) are designed to accommodate the bottom parts of the retention blades (27) of the ratchet sleeve (28) and prevent any relative rotational movement thereof (vide supra).

The outer surfaces of the short walls (84) of the engagement pockets (83) serve as "stop faces", interacting with the "set stop face" (29) and "end of dose stop face" (30) of the cylindrical body to limit the rotation of the dial unit (4) relative to the cylindrical body (3).

One of the engagement pockets defines a retaining channel (35) for the lower end of the dial spring (34) in its curved inner wall (85). The retaining channel (35) is bevelled at its upper corners to aid insertion of the dial spring (34). The lower end of dial spring (34) is rotationally restricted by the retaining channel (35) and by the stop face (72A) of a retention blade (27) of the ratchet sleeve (28), within its engagement pocket (83) of the dial unit (4).

The circular base (81) of the dial unit (4) comprises a short cylindrical wall (86) rising near its centre. This short cylindrical wall (86) fits snugly inside the inner cylindrical wall (33) depending from the inner platform (32) of the cylindrical body (3). The inner surface of circular base (81) faces the end of the inner cylindrical wall (33) of the cylindrical body (3) and prevents upward movement of the dial unit (4) relative to the cylindrical body (3).

Towards to the top of the outer cylindrical wall (82) on its inner surface, there are two diagonally opposed cylindrical body retaining clips (87). These are located on a diagonal approximately orthogonal to that on which the engagement pockets (83) are located.

The retaining clips (87) of the dial unit (4) clip over the dial sleeve rib (24) of the cylindrical body (3) to hold the dial unit (4) axially onto the cylindrical body (3).

The dial unit (4) may be turned counter-clockwise, to dispense the composition contained within the refill cartridge (12). Turning the dial unit (4) causes the ratchet sleeve (28) to turn as the two are rotationally fixed by means of the retention blades (27) protruding downwards from the ratchet sleeve (28) which interact with the engagement pockets (26) in the dial unit (4). The dial unit (4) and the ratchet sleeve (28) may together be viewed as the drive assembly for the dispenser (1).

When the drive assembly is in its most clockwise position, the drive assembly is said to be in its "rest position". When the drive assembly (100) is in its most counter-clockwise position, the drive assembly is said to be in its "advance position". The drive assembly is sprung biased via the dial spring (34) towards its rest position. A user effort must be applied to rotate the drive assembly to its advance position.

In the rest position, the advancing ratchets (75) sit in slight axial clearance of the advancing teeth (62) of the plunger (47). As the drive assembly is rotated counter-clockwise (towards its advance position), each advancing ratchet (75) will engage with an advancing tooth (62) on the plunger (47). As rotation continues, the advancing tooth (75) engaged is forced upwards by the advancing ratchet (75), together with the plunger as a whole. This forces the plunger (47) to move upwards, together with its boss (59), the drive face (60) of which acts upon the moveable piston seal of the refill cartridge (12) and thereby forces this upwards as well. The composition in the refill cartridge (12) is thus forced through the aperture (8) in the applicator head (2) onto the applicator upper surface (6), from whence it is applied.

The non-return ratchets (76) of the ratchet sleeve (28) engage with the non-return teeth (63) on the plunger (47) to prevent downward travel of the plunger (47). As the drive assembly approaches the advance position, the non-return ratchets (76) deflect outwards and snap over the next non-return tooth (63) on the plunger (47).

When the advance position is reached, each advancing ratchet (75) has advanced the drive face (60) of the plunger (47) by an amount equating to a full dose of the composition contained within the refill cartridge (12). Further counter-clockwise rotation of the advancing ratchets (75) is prevented by the interaction between the "stop faces" (30 and 84 respectively) of the cylindrical body (3) and the dial unit (4).

When the drive assembly is rotated back to its rest position by the dial spring (34), the non-return teeth (63) of the plunger (47) relax back slightly onto the non-return ratchets (76) and each advancing ratchet (75) snaps over the next advancing tooth (62).

Doses can continue to be dispensed by the method described until the advancing ratchets (75) have no more advancing teeth (62) to advance. The dial unit (4) may still be rotated at such stage, but no further advancement of the plunger (47) will occur.

FIG. 19 illustrate aspects of the refill cartridge (12) used as a replaceable part of the present dispenser (1). The position of the refill cartridge (12) in relation to the other components of the dispenser (1) is illustrated in FIG. 4.

The refill cartridge (12) sits within the refill holder (39). It comprises a refill body (88) and a refill piston (89).

The refill body (88) comprises a cylindrical barrel (90) and an annular applicator head reaction face (91) protruding from a top face (92) of the refill body (88). The annular applicator head reaction face (91) defines at its centre an inwardly tapering tubular orifice (93). This tubular orifice (93) is designed to seal against the refill sealing projection (11) depending from the centre of the underside of the applicator head (2), when all relevant components are assembled.

When relevant components are assembled, the applicator head reaction face (91) of the refill cartridge (12) presses against ribs (94) protruding radially from the refill sealing projection (11) at the centre of the underside of the applicator head (2), these ribs (94) being illustrated in FIG. 6.

When relevant components are assembled, the refill clips (14) on the inner edge of the refill retaining projection (13) clip under a retaining lip (95) present on the outer surface of the cylindrical barrel (90) of the refill cartridge (12). This gives a light axial binding of the refill cartridge (12) to the applicator head (2) and enables the refill cartridge (12) to be later removed from the refill holder (39) without the consumer needing to touch the potentially exposed composition at the end of the refill cartridge (12) itself. Towards the top of the cylindrical barrel (90) of the refill cartridge (12), but below the aforementioned retaining lip (95), there is an annular bead (96) projecting outwards from the barrel's surface. This serves to prevent the refill cartridge (12) being inserted the wrong way into the refill holder (39) by consumers.

The cross-sectional element of the refill piston (89) is hatched in FIG. 19. It is inserted into the refill body (88) after the two components have been independently manufactured.

When relevant components are assembled and the dispenser (1) is actuated, the refill piston (89) is forced upwards by the drive face (60) at the top of the cylindrical boss (59) of the plunger (47). This in turn forces the composition within the refill cartridge (12) out through the central aperture (8) in the applicator head (2) and onto the surface (6) thereof.

The refill cartridge (12) typically has a cap (97) (not illustrated) associated with it, said cap (97) being for sealing the refill cartridge (12) during transit prior to its loading into the dispenser (1).

When the refill cartridge (12) requires replacing, this is easily achieved. The user first rotates the applicator head (2) counter-clockwise by approximately 30°. This disengages the bayonet lugs (17) of the applicator head (2) from their bayonet tracks (20) on the outer surface of the applicator head sleeve (18) and allows the applicator head (2) and associated refill cartridge (12) to be lifted clear of the cylindrical body (3) and associated refill holder (39). The refill cartridge (12) is held on the applicator head (2) by the refill retaining projection (13) and its associated refill clips (14), but can be easily removed by hand.

When the applicator head (2) is rotated anticlockwise to disengage the bayonet lugs (17) from the bayonet tracks (20), there is a secondary effect upon the plunger (47). The applicator head (2) is rotationally locked to refill holder (39) by means of the engagement tabs (15) of the former interacting with the engagement pockets (52) of the latter. Further, the refill holder (39) is rotationally locked to the plunger (47) by means of the plunger splines (52A) of the former being inserted into longitudinal recesses (53) in the latter. Thus, turning the applicator head (2) turns the plunger (47).

When the plunger (47) is turned counter-clockwise by the refill holder (39) by approximately 30° from its rest position, the non-return ratchets (76) on the ratchet sleeve (28) become disengaged from the non-return teeth (63) on the plunger (47). At this rotational orientation, the advancing ratchets (75) and non-return ratchets (76) on the ratchet sleeve (28) are aligned with the recessed sections (58A) of the plunger (47), the former being aligned with those parts of the recessed sections (58A) that bears no teeth. This enables the plunger (47) to "re-set" by sliding vertically down with respect to the ratchet sleeve (28). This re-setting is assisted by the reset spring (57), the top end of which is coiled around the recessed outer section (56) at the base of refill holder (39). At its lower end the reset spring (57) presses downwards on top inner surface of the reset stop face (61) at the base of the plunger (47).

When the applicator head (2) is replaced and turned clockwise to lock and set the dispenser (1) ready for use, the ratchet sleeve (28) is re-positioned at the top of the plunger (47) ready for re-engagement therewith.

The over-cap (5) has inwardly projecting tongues (not illustrated) designed to protrude into the annular recess (8) in the peripheral skirt (7) of the applicator head (2) and thereby aid its retention thereon.

The invention claimed is:

1. A product comprising a composition and a dispenser therefor, the composition being a gel, cream or soft solid of viscosity from 3000 mPa·s to 5200 mPa·s at a shear rate of 16/s comprising a non-pore blocking inhibitor of perspiration and the dispenser comprising a dome-shaped applicator surface of radius of curvature decreasing from a maximum of from 25 to 60 mm at its top/centre to a value of from 75 to 95% of its maximum value at, a distance of 1 cm from its top/centre.

2. A product according to claim 1, wherein radius of curvature of the dome-shaped applicator surface decreases to a value of from 10 to 25% of its maximum at a distance between 1.5 cm and 2.5 cm from its top/centre.

3. A product according to claim 1, wherein the diameter of the dome-shaped applicator surface is from 3 cm to 6 cm.

4. A product according to claim 1, comprising an aperture in the applicator surface for release of the composition from an internally contained reservoir.

5. A product according to claim 4 comprising an over-cap for the applicator surface that serves to reduce evaporative loss from the composition through the aperture in the applicator surface.

6. A product according to claim 4, comprising a drive mechanism for forcing the composition from its reservoir onto the applicator surface, said drive mechanism comprising a dial unit and a plunger, the dial unit being rotated to advance the plunger, which in turns advances the composition onto the applicator surface through the aperture therein.

7. A product according to claim 6, wherein rotation of the dial unit in a first direction advances the plunger axially upwards, the plunger acting upon a piston seal at the base of a replaceable cartridge containing the composition and thereby forcing the contained composition upwards and outwards through the aperture in the applicator surface; rotation of the dial unit in a second direction, counter to the first, rotationally re-setting the dial unit relative to the plunger in readiness for a further advancement of the plunger, rotation in the second direction not causing significant axial movement of the plunger.

8. A product according to claim 6, comprising stop faces that restrict rotational movement of the dial unit in its first direction to less than 180°.

9. A product according to claim 4, wherein the reservoir is a replaceable refill cartridge.

10. A product according to claim 9, comprising a passageway from the replaceable refill cartridge to the applicator surface, terminating at the aperture in the applicator surface and having a minimum cross-sectional area of at least 1.0 mm$^2$.

11. A product according to claim 1, wherein the composition is transferred from onto the applicator surface in unit doses.

12. A product according to claim 1, wherein the non-pore blocking inhibitor of perspiration is an anticholinergic agent.

13. A product according to claim 1, wherein the non-pore blocking inhibitor of perspiration is oxybutynin.

14. A product according to claim 1, wherein the composition comprises from 1 to 5% by weight of the non-pore blocking inhibitor of perspiration.

15. A product according to claim 1, wherein the viscosity of the composition is from 3500 mPa·s to 5000 mPa·s a shear rate of 16/s.

16. A product according to claim 15, wherein the viscosity of the composition is from 4000 mPa·s to 4600 mPa·s a shear rate of 16/s.

17. A Product according to claim 1, for use in treating perspiration, in particular excessive perspiration.

18. A product according to claim 1, wherein the replaceable cartridge may be removed from the outer body or a refill holder within the outer body by means of a removable applicator head bearing the convex applicator surface at its top.

19. A cosmetic method of controlling perspiration, in particular excessive perspiration, wherein the method comprises the use of a product according to claim 1.

* * * * *